(12) United States Patent
Helson

(10) Patent No.: US 7,805,255 B2
(45) Date of Patent: *Sep. 28, 2010

(54) DERIVING FIXED BOND INFORMATION

(75) Inventor: Harold E. Helson, Arlington, MA (US)

(73) Assignee: CambridgeSoft Corporation, Cambridge, MA (US)

( * ) Notice: Subject to any disclaimer, the term of this patent is extended or adjusted under 35 U.S.C. 154(b) by 289 days.

This patent is subject to a terminal disclaimer.

(21) Appl. No.: 11/939,101

(22) Filed: Nov. 13, 2007

(65) Prior Publication Data

US 2008/0183400 A1    Jul. 31, 2008

Related U.S. Application Data

(63) Continuation of application No. 09/506,717, filed on Feb. 18, 2000, now Pat. No. 7,295,931.

(60) Provisional application No. 60/120,614, filed on Feb. 18, 1999.

(51) Int. Cl.
*G01N 5/02* (2006.01)

(52) U.S. Cl. .............................. 702/23; 702/22; 702/27; 702/183

(58) Field of Classification Search ............... 702/19, 702/20, 22, 27, 179, 182, 183; 395/500.05; 435/4, 6; 703/11
See application file for complete search history.

(56) References Cited

U.S. PATENT DOCUMENTS

| | | | |
|---|---|---|---|
| 4,473,890 A | 9/1984 | Araki et al. | |
| 4,747,059 A | 5/1988 | Hirayama et al. | |
| 4,811,217 A | 3/1989 | Tokizane et al. | |
| 4,908,781 A | 3/1990 | Levinthal et al. | |
| 5,025,388 A | 6/1991 | Cramer, III et al. | |
| 5,157,736 A | 10/1992 | Boyer et al. | |
| 5,249,137 A | 9/1993 | Wilson et al. | |
| 5,345,516 A | 9/1994 | Boyer et al. | |
| 5,379,234 A | 1/1995 | Wilson et al. | |
| 5,418,944 A | 5/1995 | DiPace et al. | |

(Continued)

FOREIGN PATENT DOCUMENTS

JP        401161578        6/1989

(Continued)

OTHER PUBLICATIONS

Anonymous, "Databases Added to ChemWeb", *Information Today*, 2 pages, May 1998.

(Continued)

*Primary Examiner*—Hal D Wachsman
*Assistant Examiner*—Felix E Suarez
(74) *Attorney, Agent, or Firm*—Wilmer Cutler Pickering Hale & Dorr LLP.

(57) ABSTRACT

Fixed bond information is derived. A fixed bond representation of a chemical structure is derived from a delocalized representation. A path is conceptually traced through the represented structure and an examination is conducted, for each atom, of each possible electronic and bonding state that is consistent with what has come before along the path. A result is found by extensively or exhaustively examining all possible states and orders in a semi-recursive procedure that is directed early towards likely answers. If there is more than one possible solution, the best solution is chosen by use of a rating function.

15 Claims, 37 Drawing Sheets

U.S. PATENT DOCUMENTS

| | | | |
|---|---|---|---|
| 5,424,963 | A | 6/1995 | Turner et al. |
| 5,434,796 | A | 7/1995 | Weininger |
| 5,448,498 | A | 9/1995 | Namiki et al. |
| 5,461,580 | A | 10/1995 | Facci et al. |
| 5,486,995 | A | 1/1996 | Krist et al. |
| 5,577,239 | A | 11/1996 | Moore et al. |
| 5,619,421 | A | 4/1997 | Venkataraman et al. |
| 5,699,268 | A | 12/1997 | Schmidt et al. |
| 5,740,072 | A | 4/1998 | Still et al. |
| 5,740,425 | A | 4/1998 | Povilus |
| 5,778,377 | A | 7/1998 | Marlin et al. |
| 5,841,678 | A | 11/1998 | Hasenberg et al. |
| 5,851,272 | A | 12/1998 | Vicenzi |
| 5,854,992 | A | 12/1998 | Shakhnovich et al. |
| 5,874,564 | A | 2/1999 | Ecker et al. |
| 5,940,807 | A | 8/1999 | Purcell |
| 5,950,192 | A | 9/1999 | Moore et al. |
| 5,956,711 | A | 9/1999 | Sullivan et al. |
| 5,978,804 | A | 11/1999 | Dietzman |
| 5,978,848 | A | 11/1999 | Maddalozzo, Jr. et al. |
| 5,980,096 | A | 11/1999 | Thalhammer-Reyero |
| 6,007,691 | A | 12/1999 | Klock, Jr. |
| 6,014,449 | A | 1/2000 | Jacobs et al. |
| 6,023,659 | A | 2/2000 | Seilhamer et al. |
| 6,023,683 | A | 2/2000 | Johnson et al. |
| 6,038,562 | A | 3/2000 | Anjur et al. |
| 6,055,516 | A | 4/2000 | Johnson et al. |
| 6,061,636 | A | 5/2000 | Horlbeck |
| 6,081,789 | A | 6/2000 | Purcell |
| 6,119,104 | A | 9/2000 | Brumbelow et al. |
| 6,125,383 | A | 9/2000 | Glynias et al. |
| 6,128,582 | A | 10/2000 | Wilson et al. |
| 6,128,619 | A | 10/2000 | Fogarasi et al. |
| 6,178,384 | B1 | 1/2001 | Kolossvary |
| 6,185,506 | B1 | 2/2001 | Cramer et al. |
| 6,185,548 | B1 | 2/2001 | Schwartz et al. |
| 6,189,013 | B1 | 2/2001 | Maslyn et al. |
| 6,199,017 | B1 | 3/2001 | Tomonaga et al. |
| 6,219,622 | B1 * | 4/2001 | Schmidt ............... 702/27 |
| 6,226,620 | B1 | 5/2001 | Oon et al. |
| 6,236,989 | B1 | 5/2001 | Mandyam et al. |
| 6,240,374 | B1 | 5/2001 | Cramer et al. |
| 6,246,410 | B1 | 6/2001 | Bergeron et al. |
| 6,256,647 | B1 | 7/2001 | Toh et al. |
| 6,272,472 | B1 | 8/2001 | Danneels et al. |
| 6,295,514 | B1 | 9/2001 | Agrafiotis et al. |
| 6,311,134 | B1 | 10/2001 | Sorenson |
| 6,319,668 | B1 | 11/2001 | Nova et al. |
| 6,323,852 | B1 | 11/2001 | Blower, Jr. et al. |
| 6,324,522 | B2 | 11/2001 | Peterson et al. |
| 6,326,962 | B1 | 12/2001 | Szabo |
| 6,332,138 | B1 | 12/2001 | Hull et al. |
| 6,341,314 | B1 | 1/2002 | Doganata et al. |
| 6,453,064 | B1 | 9/2002 | Aikawa et al. |
| 6,505,172 | B1 | 1/2003 | Johnson et al. |
| 6,519,611 | B1 | 2/2003 | Zong et al. |
| 6,542,903 | B2 | 4/2003 | Hull et al. |
| 6,571,245 | B2 | 5/2003 | Huang et al. |
| 6,584,412 | B1 | 6/2003 | Brecher |
| 6,618,852 | B1 | 9/2003 | van Eikeren et al. |
| 6,631,381 | B1 | 10/2003 | Couch et al. |
| 6,654,736 | B1 | 11/2003 | Ellis et al. |
| 6,665,685 | B1 | 12/2003 | Bialic |
| 6,675,105 | B2 | 1/2004 | Hogarth et al. |
| 6,678,577 | B1 | 1/2004 | Stylli et al. |
| 6,721,754 | B1 | 4/2004 | Hurst et al. |
| 6,751,615 | B2 | 6/2004 | Nisler et al. |
| 6,871,198 | B2 | 3/2005 | Neal et al. |
| 6,884,079 | B2 * | 4/2005 | Takamatsu ............... 434/278 |
| 6,884,394 | B1 | 4/2005 | Hehenberger et al. |
| 7,054,754 | B1 | 5/2006 | Brecher |
| 7,295,931 | B1 * | 11/2007 | Helson ............... 702/19 |
| 7,356,419 | B1 | 4/2008 | Culot et al. |
| 2002/0049548 | A1 | 4/2002 | Bunin |
| 2002/0165853 | A1 | 11/2002 | Gogalak |

FOREIGN PATENT DOCUMENTS

| | | |
|---|---|---|
| WO | WO-99/58474 | 11/1999 |

OTHER PUBLICATIONS

Balasubramanian, K.J., "Computer Perception of Molecular Symmetry", *J. Chem. Inf. Comput. Sci.*, vol. 35, pp. 761-770, 1995.

Balducci, R. et al., "Efficient Exact Solution of the Ring Perception Problem", *J. Chem. Inf. Comut. Sci.*, vol. 34, pp. 822-831, 1994.

Barnard, J.M., "Substructure Searching Methods: Old and New", *J. Chem. Inf. Comput. Sci.*, vol. 33, pp. 532-538, 1993.

Barsamiam, S.T. et al., "Dielectric phenomenon of living matter", *IEEE Transactions of Dielectrics and Electrical Insultation*, vol. 4, No. 5, pp. 629-643, Oct. 1997.

Bauer, J. et al., "IGOR and RAIN—The First Mathematically Based Multi-Purpose Problem-Solving Computer Programs for Chemistry and Their Use as Generators of Constitutional Formulas", *Informal Commun. Math. Chem. (MATCH)*, No. 27, pp. 31-47, 1992.

Bayada, D.M. et al., "An Algorithm for the Multiple Common Subgraph Problem", *J. Chem. Inf. Comput. Sci.*, vol. 32, pp. 680-685, 1992.

Benecke, C. et al., "MOLGEN, a generator of connectivity isomers and stereoisomers for molecular structure elucidation", *Anal. Chim. Acta*, vol. 314, pp. 141-147, 1995.

Bertrand, A. et al., "DESMOL: a Subroutine for the Generation of Molecular Structures with Stereochemical Information from Connectivity Data", *J. Chem. Res. (S)*, p. 158, 1994.

Bley, K. et al., "Constitutional Formulae generated from Connectivity Information: the Program MDRAW", *J. Chem. Res. (S)*, p. 261 1991.

Brecher, The ChemFInder WebServer: Indexing Chemical Data on the Internet:, *CHIMIA*, vol. 52, pp. 658-661, 1998.

Business Editors/Health & Medical Writers, "Janssen Selects MDL's ISIS, Relational Chemical Gateway as Informatics Foundation for High Throughout Discovery", 3 pages, Dec. 2, 1998.

Cambridge Scientific Computing, Inc., "Chem3D the Molecular Modeling System", pp. 1-337, 1990.

Carhart, R.E., "A Model-Based Approach to the Teletype Printing of Chemical Structures", *J. Chem. Inf. Comput. Sci.*, vol. 16, No. 2, pp. 82-88, 1976.

Casey et al., "Optical recognition of chemical graphics", *Proceedings of the Second International Conference on Document Analysis and Recognition*, pp. 627-631, Oct. 20-22, 1993.

Cash, "A Simple Means of Computing the Kekule Structure Count for Toroidal Polyhex Fullerenes", *J. Chem. Inf. Comput. Sci.*, vol. 38, No. 1, pp. 58-61, 1998.

Chem3D Molecular Modeling and Analysis, *User's Guide*, CS Chem 3D 4.0 for Windows and MacIntosh, CambridgeSoft Corporation, 1986-1997.

Chem3D The Molecular Modeling System Version 3.0, Cambridge Scientific Computing, Inc., 1986-1990.

ChemDraw and Chem3D version history, 8 pages of version history dating back to 1985.

ChemDraw Chemical Structure Drawing Standard, *User's Guide*, CS Chem3D 4.0 for Windows and MacIntosh, CambridgeSoft Corporation, 1986-1997.

ChemDraw Chemical Structure Drawing Standard, *User's Guide*, CS ChemDraw 4.5 for Windows and MacIntosh, CambridgeSoft Corporation, 1986-1997.

ChemDraw Chemical Structure Drawing Standard, *User's Guide*, CS ChemDraw Pro Version 4.0 for Microsoft Windows and Apple MacIntosh, CambridgeSoft Corporation, 1986-1996.

Cheminovation Software, "Chemistry 4-D Draw", *User's Guide*, pp. 1-61, 1997.

Cooke-Fox et al., "Computer Translation of IUPAC Systematic Organic Chemical Nomenclature. 1.Introduction and Background to a Grammer-Based Approach", *J. Chem. Inf. Comput. Sci.*, vol. 29, pp. 101-105, 1989.

Cooke-Fox et al., "Computer Translation of IUPAC Systemic Organic Chemical Nomenclature.3.Syntax Analysis and Semantic Processing", *J. Chem. Inf. Comput. Sci.*, vol. 29, pp. 112-118, 1989.

Cooke-Fox et al., "Computer Translation of IUPAC Systematic Organic Chemical Nomenclature.4.Concise Connection Tables to Structure Diagrams", *J. Chem. Inf. Comput. Sci.*, vol. 30, pp. 122-127, 1990.

Cooke-Fox et al., "Computer Translation of IUPAC SYstematic Organic Chemical Nomenclature.5.Steroid Nomenclature", *J. Chem. Inf. Comput. Sc.*, vol. 30, pp. 128-132, 1990.

Cooke-Fox et al., "Computer Translation of of IUPAC Systematic Organic Chemical Nomenclature.2.Development of a Formal Grammar", *J. Chem. Inf. Comput. Sci..*, vol. 29, pp. 106-112, 1989.

Cooke-Fox et al., "From names to diagrams—by computer", *Chemistry in Britain*, pp. 467-471, 1985.

CRC Handbook of Chemistry and Physics, Student Edition, 76th Edition, Section 2, pp. 2-22 through 2-26, 1996-1996.

CS ChemDraw for Apple MacIntosh, *Quick Reference*, CambridgeSoft Corp., 1986-1996.

CS ChemFinder Searching and Information Integration, *User's Guide*, CS ChemFinder Pro and CS ChemFinder, Version 2.0 for Apple MacIntosh, CambridgeSoft Corporation, 1991-1995.

CS Chemfinder, "The ChemFinder WebServer: Indexing Chemical Data on the Internet", http://web.archive.org.web/19990417145549/chemfinder.camsoft.com/chimia.html, Sep. 16, 2006, 12 pages.

CSC Chem3D Molecular Modeling and Analysis, *Tutorial*, CSC Chem3D and CSC Chem 3D Plus, Version 3.1 for Apple MacIntosh, Cambridge Scientific Computing, Inc., 1986-1993.

CSC ChemDraw Chemical Structure Drawing Standard, *User's Guide*, CSC ChemDraw and CSC ChemDraw Plus Version 3.0 for Apple MacIntosh, CambridgeSoft Corporation, 1986-1996.

CSC Chemical Finder Chemical Information Management, *User's Guide*, Version 1.0 for Apple MacIntosh, Cambridge Scientific Computing, Inc., 1991-1992.

Dalby, J. et al., "Description of several Chemcial Structure File Formats Used by Computer Programs Developced at Molecuar Design Limited", *J. Chem. Inf. Comput. Sci.*, vol. 32, pp. 244-255, 1992.

Dittmar, P.G. et al., "An Algorithmic Computer Graphics Program for Generating Chemical Structure Diagrams", *J. Chem. Inf. Comput. Sci.*, vol. 17, No. 3, pp. 186-192, 1977.

Downs, G.M. et al., "Review of Ring Perception Algorithms for Chemical Graphs", *J. Chem. Inf. Comput. Sci.*, vol. 29, pp. 172-187, 1989.

Ertl, P. et al., "WWW-Based Chemical Information System", *Journal of Molecular Structure (Theochem)*, vol. 449, p. 113-129, Dec. 8, 1997.

Fan et al., "Detection of constitutionally equivalent sites from a connection table", *J. Chem. Inf. Comput. Sci.*, VVOl. 36, pp. 654-659, 1996.

Figueras, J., "Ring Perception Using Breadth-First Search", *J. Chem. Inf. Comput. Sci.*, vol. 36, p. 986-991, 1996.

Frerejacque, M., "No. 108—Condensation d'une molecule organique", *Bull. Soc. Chim. Fr., (Memoires)*, vol. 5, pp. 1008-1011, 1939.

Gelin, B. R. et al., "Inventory Tracking and ChemOffice: CIS Pro Chemical Inventory Package Connects with CS ChemOffice," CambridgeSoft News, Press Release, Aug. 24, 1998, 2 pages.

Gelin, B. R., "ChemACX Chemical Database: Search Over 100 Leading Catalogs on your Desktop or on the WWW," CambridgeSoft News, Press Release, Jan. 18, 1999, 3 pages.

Gelin, B.R., "CS ChemInfo WebServer: Subscription Services Offer WWW Substructure Searching," CambridgeSoft News, Press Release, Aug. 24, 1998, 2 pages.

Glendening et al., "Natural Resonance Theory: I. General Formalism", *Journal of Computational Chemistry*, vol. 19, No. 6, pp. 593-609, Apr. 30, 1998.

Gothe, S.A. et al., "Computer-Assisted Mechanistic Evaluation of Organic Reactions. 22. The Generation and Use of Three-Dimensional Structures", *J. Org. Chem.*, vol. 58, pp. 5081-5094, 1993.

Graovac et al., "Kekule Index for Valence Bond Structures of Conjugated Polycyclic Systems", *Journal of the American Chemical Society*, vol. 95, No. 19, pp. 6267-6273, 1973.

Helson et al., "Computer-Assisted Mechanisitic Evaluation of Organic Reactions. 25. Structure Diagram Positioning", *J. Chem. Inf. Comput. Sci.*, vol. 34, p. 962, 1993.

Helson, "Simulation of Carbene Chemistry and Other Problems in Computer-Assisted Organic Synthesis", *Thesis*, Purdue University, 1993.

Helson, "Structure Diagram Generation", *Reviews in Computational Chemistry*, vol. 13, Ch. 6, pp. 313-398, 1999.

Hu et al., "Computer perception of topological symmetry by all-paths algorithm", Abstract, *Chemometrics and Intelligent Laboratory Systems*, 45, pp. 317-322, Jan. 1999.

Hyde, E. et al., "Structure Display", *J. Chem. Doc.*, vol. 8, No. 3., pp. 138-146, 1968.

Ihde, A., "The Development of Modern Chemistry", The University of Wisconsin, Dover Publications, pp. 305-309, NY, 1984.

Ihlenfeldt et al., *Journal of Chemical Information and Computer Sciences*, vol. 35, No. 4, Jul.-Aug. 1995 (Abstract Only).

Ihlenfeldt, W.D. et al., "Beyond the Hyperative Molecule: Search, Salvage and Visualization of Chemical Information from the Internt", *Pacific Symposium on Biocomputing '96,,* vol. SYMP.1, pp. 384-398, Jan. 3, 1996.

Ihlenfeldt, W.W. et al., "Augmenting Connectivity Information by Compound Name Parsing: Automatic Assignment of Stereochemistry and Isotope Labeling", *J. Chem. Inf. Comput. Sci.*, vol. 35, pp. 663-674, 1995.

Information Today, "ISI develops electronic Index Chemicus", Medford, vol. 10, Iss. 5, p. 64, May 1993.

Jorgensen, W.L. et al., "CAMEO: a program for the logical prediction of the products of organic reactions", *Pure App.l. Chem.*, vol. 62, pp. 1921-1932, 1990.

Judson, R., "Genetic Algorithms and Their Use in Chemistry", *Reviews of Computational Chemistry*, Ch. 1, vol. 10, pp. 1-73, 1997.

Kirby et al., "Computer Translation of IUPAC Systematic Organic Chemical Nomenclature. 6. (Semi) Automatic Name Correction", *J. Chem. Inf. Comput. Sci.*, vol. 31, pp. 153-160, 1991.

Lieth, C.v.d. et al., "Rings—a general program to build ring systems", *J. Mol. Graphics*, vol. 2, pp. 117-123, 1984.

Lipkowitz et al., "Chapter 6. Structure Diagram Generation", *Reviews in Computational Chemistry*, vol. 13, pp. 313-398, 1999.

Molchanova, M.S. et al., "Computer Generation of Molecular Structures by the SMOG Program", *J. Chem. Inf. Comput. Sci.*, vol. 36, pp. 888-899, 1996.

Morikawa, "Enumeration of Kekule Structures in Polyradical Polyhexes", *Computers Chem.*, vol. 20, No. 2, pp. 159-165, 1996.

Morrison et al., "Structure and Properties", *Organic Chemistry, Third Edition*, pp. 4-8, Copyright 1973.

Morrison et al., *Organic Chemistry, Third Edition*, p. 324, Copyright 1973.

Morrison et al., *Organic Chemistry, Third Edition*, pp. 261 and 1011, Copyright 1973.

New Riverside University Dictionary, Riverside Publishing Company, Boston, MA, p. 783, 1984.

Notess, G.R., "Offspring of PACS: Local databases on the net", *Database, Weston*, 4 pages, Jun. 1993.

PR Newswire, New York, "Fisher Scientific Adopts Standards: New Electronic Commerce Web Site Among the First to Embrace Open Buying on the Internet Standards", 2 pages, Feb. 9, 1998.

PR Newswire: Judy Hunter, "CAS and Dialog agree to publish new standard", New York, Sec. 1, p. 1 (2 pages total), Sep. 29, 1994.

Rayner, J.D. et al., "A Concise Connection Table Based on Systematic Nomenclatural Terms", *J. Mol. Graphics*, vol. 1, pp. 108-111, 1983.

Razinger et al., "Graph Automorphism Perception Algorithms in Computer-Enhanced Structure Elucidation", *J. Chem. Inf. Comput. Sci..*, vol. 33, pp. 197-201, 1993.

Registry (Dictionary Searching) STN Database Summary Sheet, Revised, Chemical Abstracts Services, pp. 1-10, Mar. 1997.

Rubenstein, S., "ChemDraw Professional Desktop Publishing for Chemists", Version 2.0 Cambridge Scientific Computing, Inc., 1985-1988.

Ruiz et al., "Error Detection, Recovery, and Repair in the Translation of Inorganic Nomenclatures. 1. A Study of the Problem", *J. Chem. Inf. Comput. Sci..*, vol. 36, No. 1, pp. 16-24, 1996.

Rusinko, A. et al., "Using CONCORD to Construct a Large Database of Three-Dimensional Coordinates from Connection Tables", *J. Chem. Inf. Comput. Sci.*, vol. 29, p. 251-255, 1989.

Sadowski, J. et al., "Comparison of Automatic Three-Dimensional Model Builders Using 639 X-ray Structures", *J. Chem. Inf. Comput. Sci.*, vol. 34, p. 1000-1008, 1995.

Shelley, C.A. et al., "An approach to the assignment of canonical connection tables and topolgoical symmetry perception", *J. Chem. Inf. Comput. Sci.*, vol. 19, No. 4, pp. 247-250, 1979.

Shelley, C.A., "Heuristic Approach for Displaying Chemical Structures", *J. Chem. Inf. Comput. Sci.*, vol. 23, pp. 61-65, 1983.

Shmueli, U., "Simple and efficient approach to preparation of molecular drawings", *J. Mol. Graphics*, vol. 2, pp. 111-112, 1984.

Stillwell, "Computer Translation of Systematic Chemical Nomenclature to Structural Formulas—Steroids", *Journal of Chemical Documentation*, vol. 13, No. 3, pp. 107-109, 1973.

Thomson, L.G. et al., "Organic Search and Display Using a Connectivity Matrix Derived from Wiswesser Notation", *J. Chem. Doc.*, vol. 7, pp. 204-209, Nov. 1967.

Vander Stouw et al., "Automated Conversion of Chemical Substasnces Names to Atom-Bond Connection Tables", *Journal of Chemical Documentation*, vol. 14, No. 4, pp. 185-193, 1974.

Compounds into Atom-Bond Connection Tables, *Journal of Chemical Documentation*, vol. 7, No. 3, pp. 165-169, 1967.

Weininger, D., "SMILES, a Chemical Language and Information System. 1. Introduction to Methodology and Encoding Rules", *J. Chem. Inf. Comput. Sci.*, vol. 28, pp. 31-36, 1988.

Weininger, D., "Smiles. 3. Depict. Graphical Depiction of Chemical Structures", *J. Chem. Inf. Comput. Sci.*, vol. 30, pp. 237-243, 1990.

Wilder, "Net Catalog Sales", *Information Week; Manhassete*, 2 pages, Feb. 1, 1999.

Wipke, T., "AIMB: Analogy and Intelligence in Model Building. System Description and Performance Characteristics", *Computer Representation and Manipulation of Chemical Information*, pp. 147-174, Wipke et al. editors, Krieger, NY, 1981.

Wipke, W. T. et al., "Computer-Assisted Three-Dimensional Synthetic Analysis", *Tet. Comput. Method.*, vol. 1, pp. 147-174, 1988.

www.cambridgesoft.com/services/history.cfm?FID=1, printed Apr. 9, 2004, 7 pages.

www.cambridgesoft.com/services/history.cfm?FID=2, printed Apr. 9, 2004, 6 pages.

www.cambridgesoft.com/services/history.cfm?FID=3, printed Apr. 9, 2004, 3 pages.

www.cambridgesoft.com/services/history/cfm?FID=4, printed Apr. 9, 2004, 2 pages.

Zimmerman, B.L., Thesis, University of Pennsylvania, 1971.

Zipple, M. et al., "Spektren—A Computer System for the Identification and Structure Elucidation of Organic Compounds", *Anal. Chim Acta*, vol. 140, pp. 123-142, 1982.

ChemFinder, Searching and Information Integration, CS ChemFinder 4.0 for Windows and Macintosh (3.0), CambridgeSoft Corporation 1986-1997.

Figueras, J. et al., "Automorphism and Equivalence Classes", *J. Chem. Inf. Comput. Sci.*, vol. 32, pp. 153-157, (1992).

\* cited by examiner

Table 1. Selected Electronic State/Valence Distributions[a]

| Elm | Chrg | Rad | Bd#1 | Bd#2 | #Extern Bds[b] | #e's Contrib | Shorthand | Structure |
|---|---|---|---|---|---|---|---|---|
| B |    |   | 1 | 2 | 0 | 1 | [120/1]   | B-1 |
| B |    |   | 1 | 1 | 1 | 0 | [111/0]   | B-2 |
| B | -1 |   | 1 | 2 | 1 | 1 | [121/1-]  | B-3 |
| C |    |   | 1 | 2 | 1 | 1 | [121/1]   | C-1 |
| C | +1 |   | 1 | 1 | 1 | 0 | [111/0+]  | C-2 |
| C | -1 |   | 1 | 1 | 1 | 2 | [111/2-]  | C-3 |
| C |    |   | 1 | 1 | 1 | 1 | [111/1*]  | C-4 |
| C |    |   | 1 | 1 | 2 | 1 | [112/1]   | C-5 |
| N |    |   | 1 | 2 | 0 | 1 | [120/1]   | N-1 |
| N |    |   | 1 | 1 | 1 | 2 | [111/2]   | N-2 |
| N | +1 |   | 1 | 2 | 1 | 1 | [121/1+]  | N-3 |
| N | +1 |   | 1 | 1 | 1 | 1 | [111/1+*] | N-4 |
| O |    |   | 1 | 1 | 0 | 2 | [110/2]   | O-1 |
| O | +1 |   | 1 | 1 | 1 | 2 | [111/2+]  | O-2 |
| O | +1 |   | 1 | 2 | 0 | 1 | [120/1+]  | O-3 |
| P like N[c] | | | | | | | | |
| P |    |   | 1 | 2 | 2 | 1 | [122/1]   | P-1 |
| S like O | | | | | | | | |
| S |    |   | 2 | 2 | 0 | 2 | [220/2]   | S-1 |
| Cl | +1 |   | 1 | 1 | 0 | 2 | [110/2+]  | Cl-1 |
| Cl |    |   | 1 | 2 | 2 | 1 | [122/1]   | Cl-2 |
| Cl |    |   | 1 | 2 | 4 | 1 | [124/1]   | Cl-3 |

FIG. 7

Table 2. Procedure Control Flags

| Flag | Meaning |
|---|---|
| kDontAssumeImpH | Otherwise, heteroatoms might carry undrawn hydrogens. |
| kIfFailWithOneSystem_FailWithAll | If given two or more delocalized systems and one fails, the molecule is returned unchanged, and the procedure fails. |
| kDoNotCreateCharges | Do not create zwitterions, i.e., more charges than necessary to achieve the system's net charge. |
| kDoNotCreateRadicals | Do not create more than one radical. |
| kConfineChargesToHeteroatoms | All charged atoms must be heteroatoms. |
| kConfineRadicalsToHeteroatoms | All atoms with an unpaired electron must be heteroatoms. |
| kFavorMultiplyBondedHetero | When a system can support more or fewer multiple bonds, favor the form with more multiple bonds (even if it is anti-aromatic). |
| kDisfavorAntiaromaticSystems | Use this flag in conjunction with the previous. |
| kSolutionMustBeFullyAlternating | Bonds must alternate as single and double. |

FIG. 9

Table 3. Meanings of bits in the ESVD Screening Bitmask (ESB) and Atom Screening Bitmask (ASB)

| Bit # | Description |
|---|---|
| 0 | Has an internal single bond |
| 1 | Has two internal single bonds |
| 2 | Has an internal double bond |
| 3 | Has two internal double bonds |
| 4 | Has an external bond |
| 5 | Does *not* have an external bond |

| Bit # | Description |
|---|---|
| 8 | Charge = 0 |
| 9 | Charge = +1 |
| 10 | Charge = -1 |
| 11 | Charge ≠ -1 |
| 12 | Charge ≠ +1 |
| 13 | Radical present |
| 14 | Radical not present |

FIG. 11

| Action # | Action | Atom / Bond | Action # | Action | Atom or Bond |
|---|---|---|---|---|---|
| 1 | Assign ESVD | Atom 0 | 14 | Assign Bond | Bond 10 |
| 2 | Assign Bond | Bond 0 | 15 | Assign ESVD | Atom 9 |
| 3 | Assign ESVD | Atom 1 | 16 | Assign Bond | Bond 9 |
| 4 | Assign Bond | Bond 1 | 17 | Assign ESVD | Atom 8 |
| 5 | Assign ESVD | Atom 2 | 18 | Assign Bond | Bond 8 |
| 6 | Assign Bond | Bond 2 | 19 | Assign ESVD | Atom 7 |
| 7 | Assign ESVD | Atom 3 | 20 | Assign Bond | Bond 7 |
| 8 | Assign Bond | Bond 3 | 21 | Assign ESVD | Atom 6 |
| 9 | Assign ESVD | Atom 4 | 22 | Assign Bond | Bond 6 |
| 10 | Assign Bond | Bond 4 | 23 | Verify completed | Atom 4 |
| 11 | Assign ESVD | Atom 5 | 24 | Complete | --- |
| 12 | Assign Bond | Bond 5 | | | |
| 13 | Verify completed | Atom 0 | | | |

FIG. 13

Table 4. The Actions Comprising a Strategy

| Action | Applies To | Explanation |
|---|---|---|
| Assign ESVD | Atom | Find the ESVD's for the current atom that are compatible with its environment. The best one is used directly, and if there is more than one, the rest are queued. |
| Assign Bond | Bond | Assign a bond order to the current bond, consistent with the ESVD of the previous atom, i.e. the (earliest occurring) atom adjacent to the bond. (The bond's other atom has not been encountered yet, unless the bond closes a ring. Even in this case, the other atom's environment is not taken into account. It will be checked in the next Action.) |
| Verify Completed | Atom | This Action is taken just after the last bond in a ring or acyclic chain is fixed. Ordinarily the bonds of an atom are sure to be compatible with its assigned ESVD because its ESVD was picked to be compatible with the bond leading to it, and the bond leading away from it was selected to be compatible with its ESVD. However, a ring closure atom has not had its ESVD checked with respect to the ring closure bond, nor has a terminal atom in an acyclic chain. Thus, in this Action the atom is checked to verify that its final bonding environment is compatible with its ESVD. |
| Complete | -- | Signifies that the path is completed, and all atoms have been assigned compatible ESVD's and bond orders. If the net charge or radical count of the putative solution is wrong, the solution is rejected. If the solution is perfect, as defined elsewhere, it is returned directly and the procedure terminates. Otherwise, if it is the best solution yet, it displaces the previous best candidate. |

FIG. 14

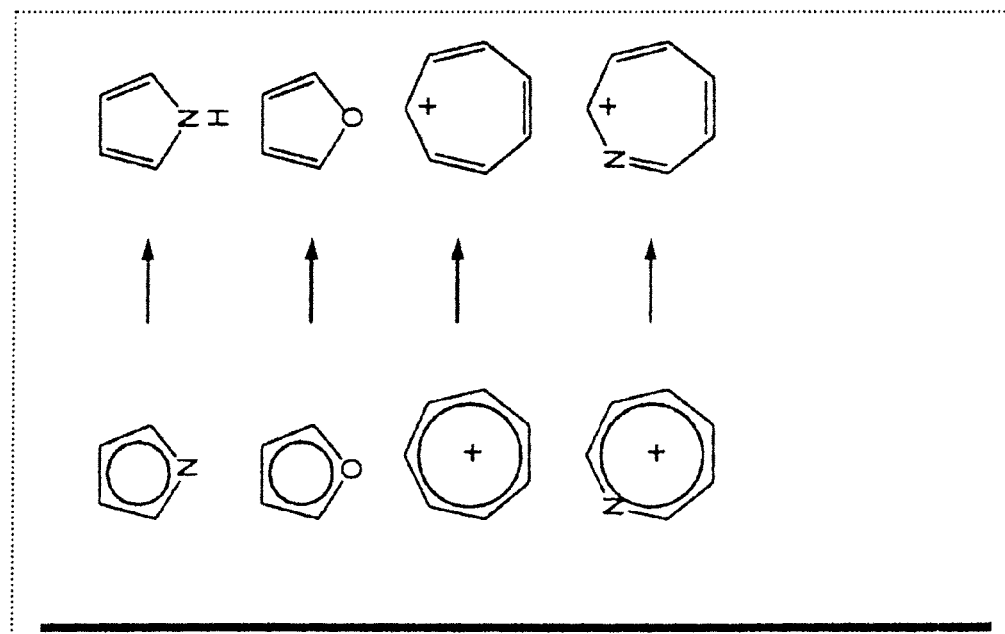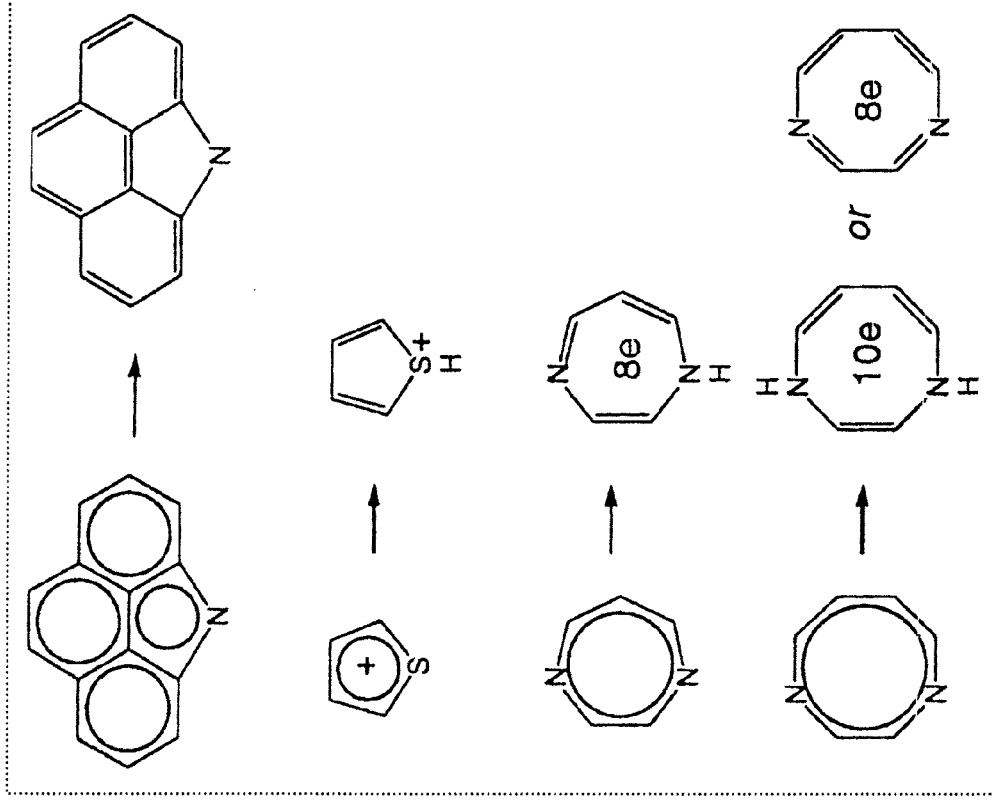
FIG. 17

/‒2000

> Identify discrete (i.e., not adjacent) delocalized systems present in the structure (step 2010).
>
>> Select any delocalized bond that has not already been treated (step 2020)
>>
>> ↓
>>
>> Add all adjacent delocalized bonds (step 2030)
>>
>> ↓
>>
>> Continue to add delocalized bonds adjacent to those just found, until no new bonds are added (step 2040)

↓

> For each of the identified delocalized systems (step 2050)
>
>> Analyze *DS* for characteristics (step 2060)
>>
>>> Note the total charge and radical count required of the pi system (step 2070)
>>>
>>> ↓
>>>
>>> Calculate the internal coordination number ("ICN") of each atom (step 2080)
>>>
>>> ↓
>>>
>>> Identify bonds in *DS* that must be fixed, as a consequence of having an adjacent fixed multiple bond (step 2090)
>>>
>>> ↓
>>>
>>> Develop a path through *DS* (step 2100)
>>>
>>> ↓
>>>
>>> Construct the strategy list (step 2110)
>>>
>>> ↓
>>>
>>> Identify ring systems (step 2120)

↓

Set the best solution ("*BS*") to "undefined" (step 2130)

Return "*Keep Trying*" (step 4270)

DERIVING FIXED BOND INFORMATION

CROSS-REFERENCE TO RELATED APPLICATIONS

This application is a continuation of U.S. patent application Ser. No. 09/506,717, filed Feb. 18, 2000, now U.S. Pat. No. 7,295,931, entitled DERIVING FIXED BOND INFORMATION, which claimed the benefit of U.S. Provisional Application Ser. No. 60/120,614 entitled REPRESENTING A CHEMICAL STRUCTURE filed on Feb. 18, 1999, both incorporated by reference herein.

BACKGROUND OF THE INVENTION

This application relates to deriving fixed bond information.

Some chemical structures may be depicted with circles or arcs instead of with alternating single and double bonds (see the leftmost structure of FIG. 1). Since a well known chemist named Auguste Kekulé suggested that double bonds were not fixed or localized, and depicted a benzene ring with a delocalizing circle instead of alternating single and double bonds, the process of perceiving aromaticity (i.e., cyclic delocalization) from a fixed-bond representation may be called "Kekulization." A Kekulé structure representation is one in which the alternating single and double bonds of the classical depiction are replaced by all single bonds, adorned by a circle or arc.

SUMMARY OF THE INVENTION

A method and a system are provided for deriving fixed bond information. In particular, a fixed bond representation of a chemical structure is derived from a delocalized representation. A path is conceptually traced through the represented structure and an examination is conducted, for each atom, of each possible electronic and bonding state that is consistent with what has come before along the path. A result is found by examining states and orders in a semi-recursive procedure that is directed early towards likely answers. If there is more than one possible solution, the best solution is chosen by use of a rating function.

The method and the system are able to handle acyclic as well as cyclic systems, organic and organometallic structures, and can produce useful results in situations involving wide ranges of ring sizes and ring systems, element types, and hybridization. All or nearly all aromatic (i.e., cyclically delocalized) systems, including such systems with hetero substituents, and cyclic systems, and mixed cyclic-acyclic systems, can be addressed effectively by the method and the system. Charged systems, and systems with unpaired electrons can be handled as well. The method and the system are able to enumerate the mesomers of a structure.

Other features and advantages will become apparent from the following description, including the drawings, and from the claims.

BRIEF DESCRIPTION OF THE DRAWINGS

FIGS. 1-6, 8, 10, 12, and 15-21 are illustrations of output produced by software.
FIGS. 7, 9, 11, and 13-14 are illustrations of computer data.
FIGS. 22, 23A-23B, 24, 25A-25C, 26A-26B, 27-30, and 31A-31C are flow diagrams of computer-based procedures.

DETAILED DESCRIPTION

Figure 1:
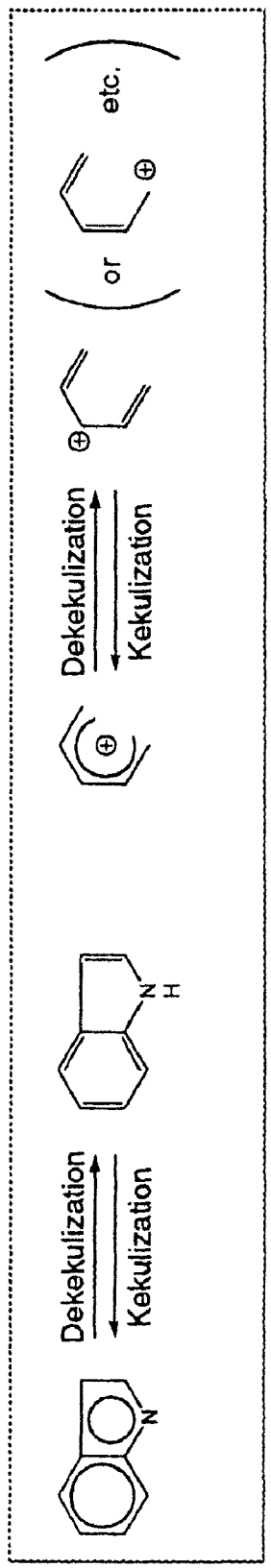

A procedure is described in detail below in which a cyclic (i.e., aromatic) or acyclic delocalized system or structure diagram is dekekulized, i.e., in which a representation having alternating single and double bonds is derived from the delocalized system (see FIG. 1). In particular, a fixed-bond ("localized-bond") representation of an organic or organometallic structure is derived from a delocalized-bond representation of the structure.

The procedure allows fixed bond representations to be made more available to readers who prefer such representations, particularly when the pertinent bonding is part of a reaction that affects the pi system. (A pi orbital is the simplest atomic orbital that is amenable to delocalization. A pi system is a collection of pi orbitals that share electrons. As used herein, "pi" also refers to d, f and any other atomic orbitals that pool electrons with at least two other atoms.)

Figure 2:
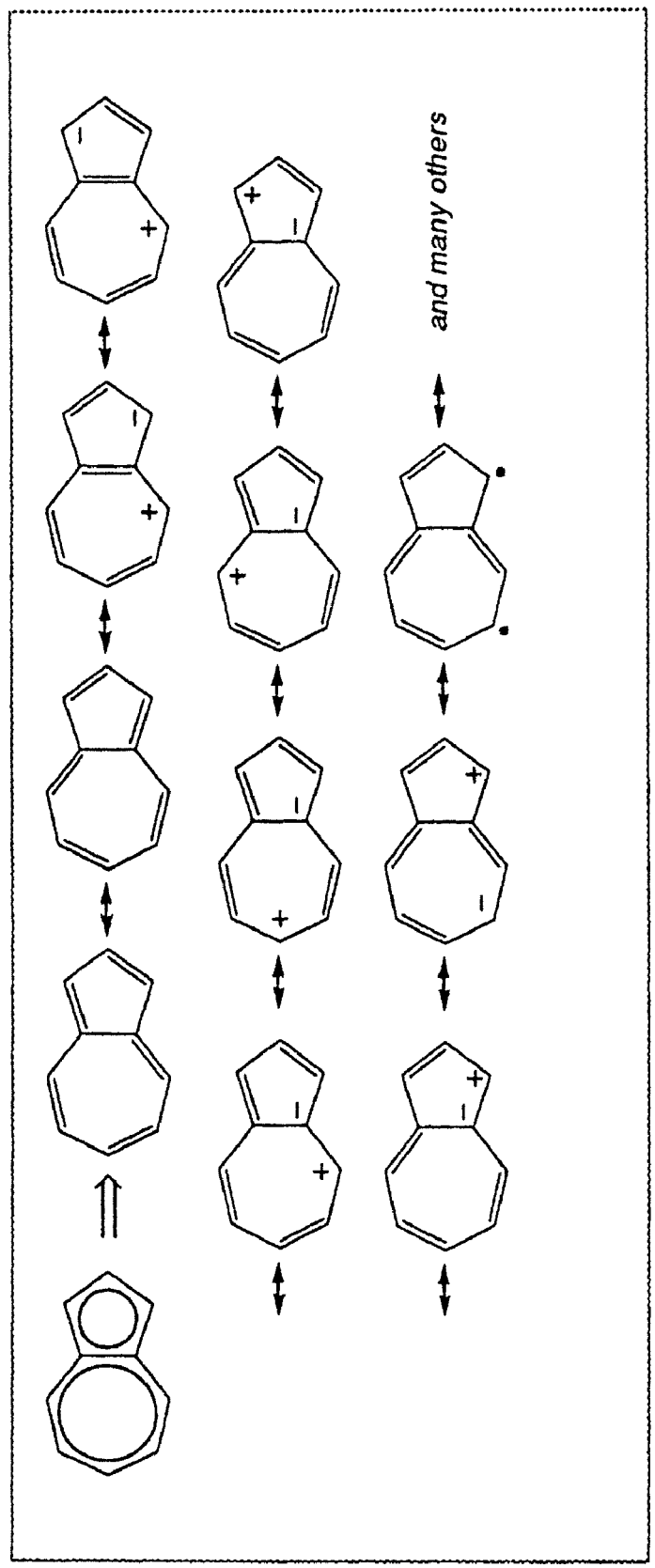

The procedure allows mesomers to be enumerated (see, e.g., FIG. 2). A mesomer is also known as a resonance structure. Mesomers are enumerated for at least two purposes: to understand delocalization and its relation to fixed bond representations and to rationalize or predict chemical reactivity.

Figure 3:
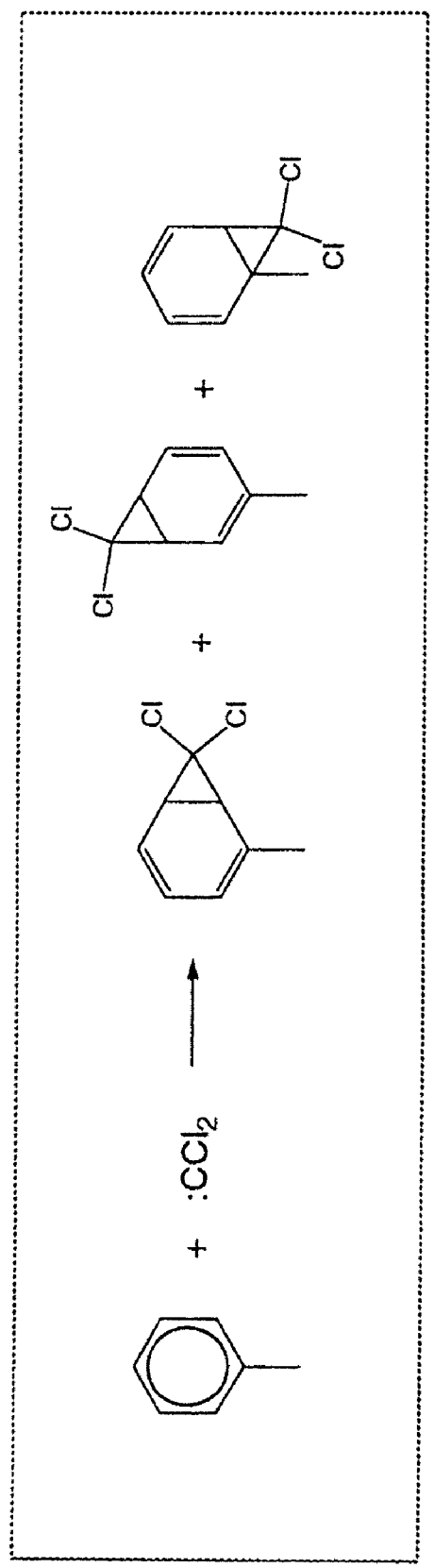
Figure 4:
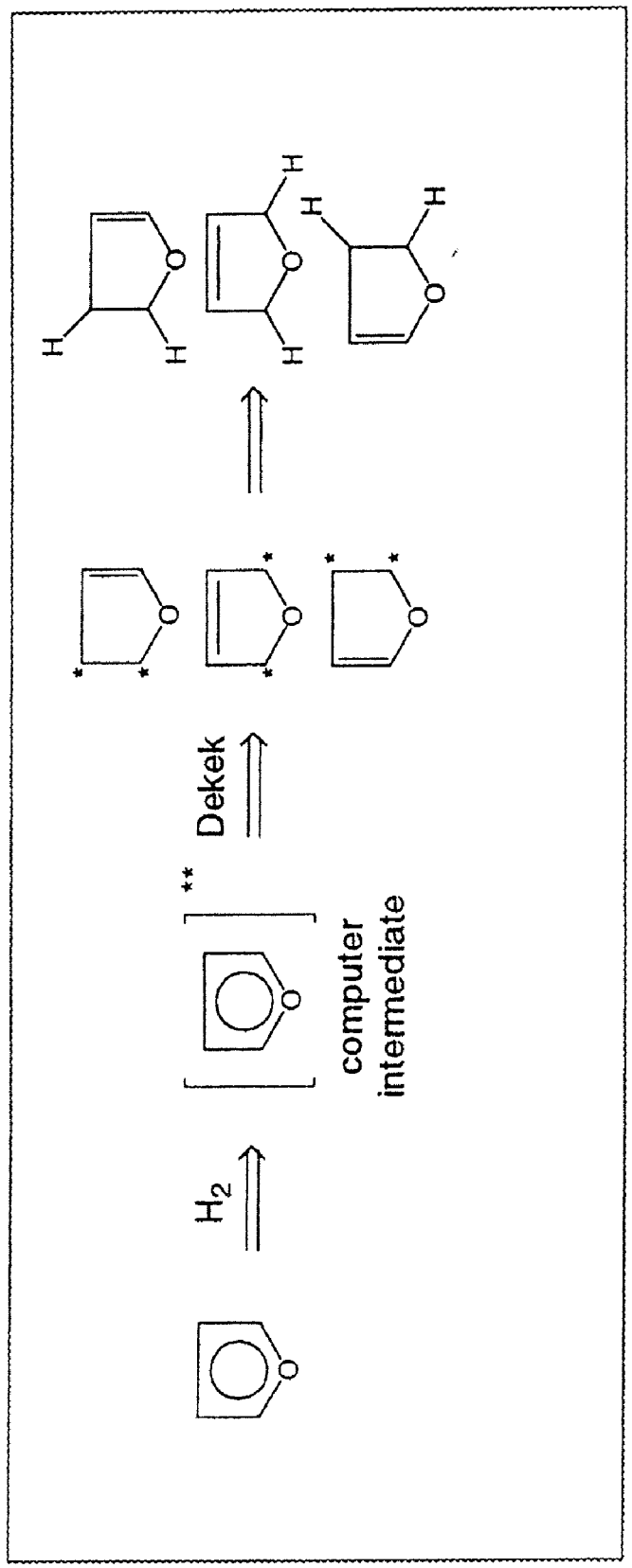

Furthermore, computer programs that predict products may need to supply bond fixation information. A carbene example is shown in FIG. 3 which demonstrates that a reaction of a pi system may entail bond fixation: all the fixed bond mesomers of toluene are enumerated; each undergoes reaction; and duplicate products, if any, are eliminated. With respect to hydrogenation, if an aromatic or delocalized acyclic system is provided, and it is known that a particular portion of hydrogen has been added, dekekulization is the first step in locating various alternative locations for the added hydrogens and the residual double bonds (see FIG. 4 which illustrates an application of dekekulization to the assignment of hydrogenation isomers).

Figure 5:
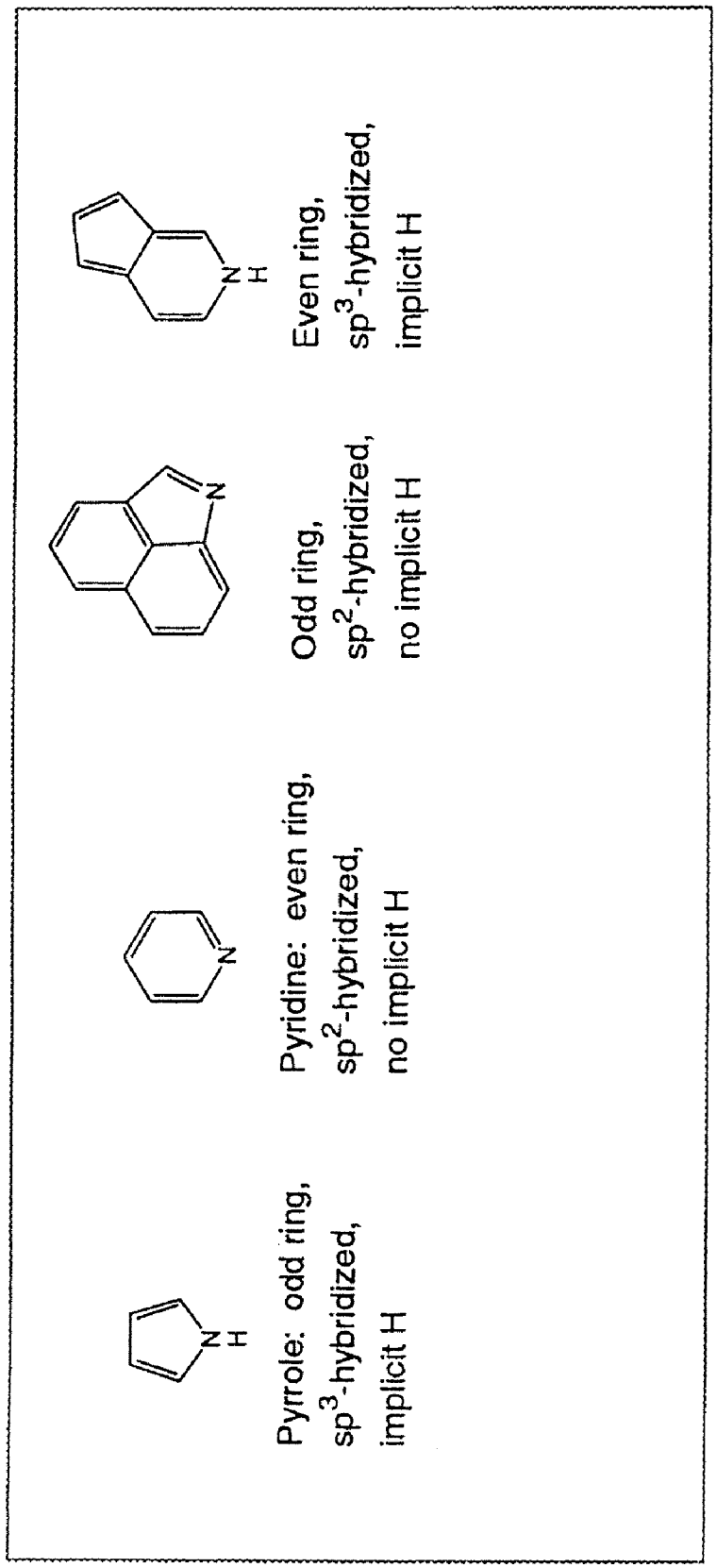

The procedure also allows determination of heteroatom hybridization and the number of "implicit" hydrogens attached to heteroatoms. If hydrogen atoms have been omitted from a drawing of a delocalized system (see, for example, the lefthand structure of FIG. 1), the procedure reveals in many or most cases the hydrogen count at each atom necessary to make chemical sense of the structure. As suggested in FIG. 5, this information is not generally apparent from simple graph theory. FIG. 5 illustrates the unpredictability of heteroelement hybridization, and resulting implicit hydrogen count. It may be desirable to generalize from pyrrole and pyridine that heteroatom hybridization follows from ring size, but such a generalization can prove unreliable, as demonstrated by the two counterexamples at right in FIG. 5.

Inferring fixed bond orders from a delocalized representation is also an important process in computer-assisted organic synthesis.

One or more of the procedures related to dekekulization as described herein may be used in or with one or more procedures described in the following United States patent applications, which are incorporated herein: METHOD, SYSTEM, AND SOFTWARE FOR DERIVING CHEMICAL STRUCTURAL INFORMATION, Ser. No. 09/502,810, filed Feb. 11, 2000, now U.S. Pat. No. 7,054,754, issued May 30, 2006, and ENHANCING STRUCTURE DIAGRAM GENERATION, Ser. No. 09/502,133, filed Feb. 11, 2000. For example, dekekulization as described herein may be used to help derive a chemical structure diagram from a chemical name.

Conceptually, in a specific embodiment of the procedure, a path is traced through the structure and, for each atom, each possible electronic and bonding state is examined that is consistent with previous results along the path. By extensively or exhaustively examining possible states and orders, the procedure is able to arrive at a fixed bond solution, if one exists.

An inspection of fixed-bond structure diagrams reveals, with respect to carbon atoms, that a pair of adjacent delocalized bonds tends to be replaced by one single and one double bond. If a carbon atom stands as a fusion atom, e.g., as one of the tertiary atoms in naphthalene, the third bond is single, and may be viewed as an appropriation of the fourth bond that otherwise would be directed outside of the delocalized system. Nitrogen, on the other hand, typically may have either two single bonds directed into the system plus a single bond externally directed, as in pyrrole, or a single and a double directed into the system, with no external bonds, as in pyridine.

In a specific implementation, in the procedure, every atom is described by a three-digit code representing a bonding environment. In many cases, carbon's code is [121], which indicates that of the two originally delocalized bonds, one becomes single and the other becomes double, and that there is one residual valence unit to be deployed either outside the system (e.g., a sigma bond) or with a third atom within the system (naphthalene). The code can be enhanced to indicate the number of pi electrons formally contributed to the delocalized system by an atom in the pertinent state. For the common carbon state, the number is one, indicated by the enhanced code [121/1].

Figure 6:
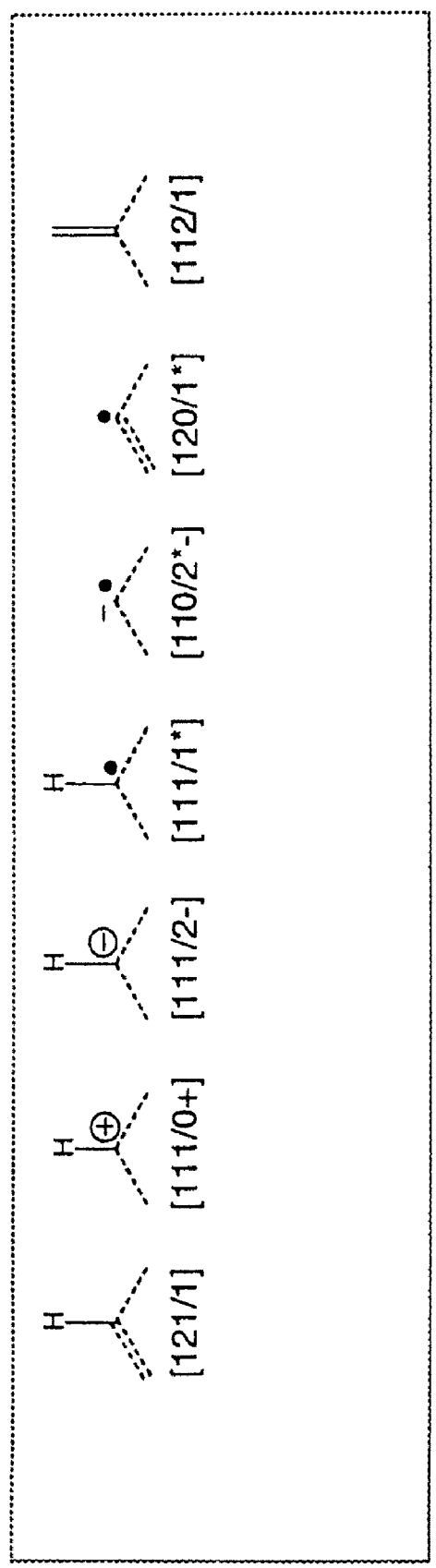
Figure 8:
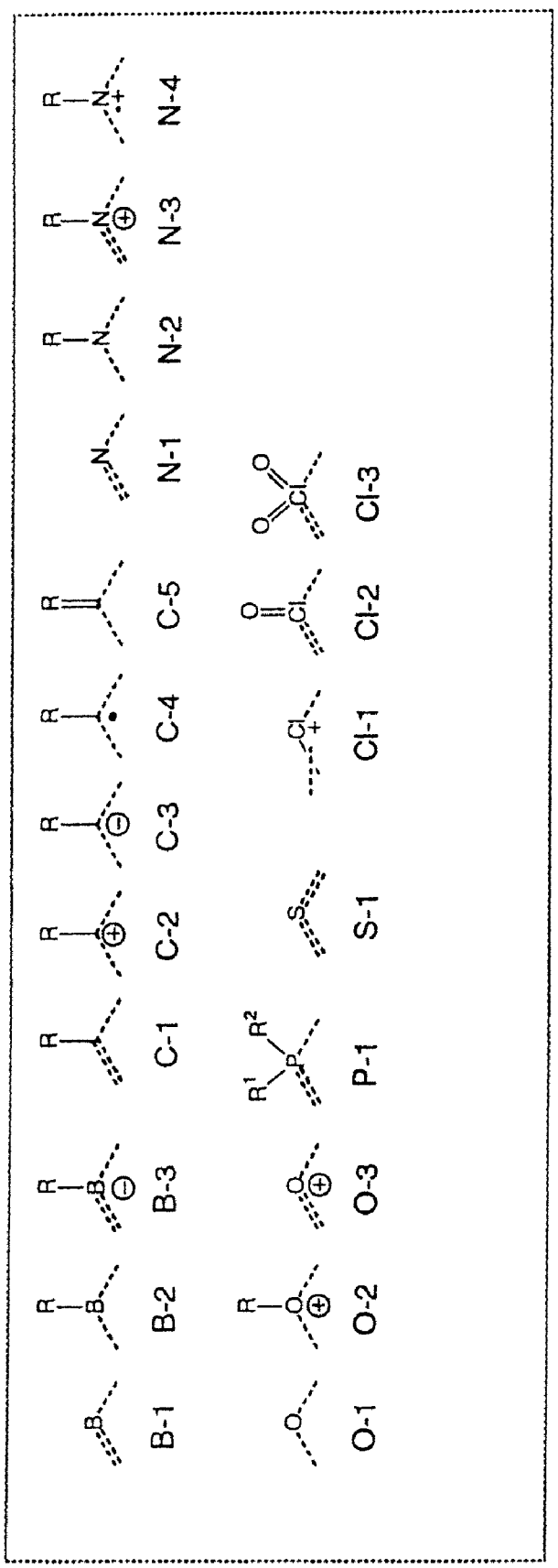

Information for an atomic environment may refer to a charge or an unpaired electron or both, in addition to the bonding information. The collection of characteristics involved is referred to hereinafter as an environment or as an electronic state and valence distribution ("ESVD"). A carbon atom as commonly encountered in organic chemistry, with two attachments that are part of the delocalized system, is found only in the environments shown in FIG. 6. In FIG. 6, which illustrates the electronic/bonding environments available to a carbon atom with two delocalized attachments, dashed bonds represent the fixed bonds that are replacing delocalized bonds. (Although neutral and fully paired, the rightmost ESVD tends to be a poor choice due to poor overlap of its pi orbital with the two delocalized attachments of interest.) Common codes for nitrogen are [111/2] (pyrrole) and [120/1] (pyridine). Prevalent atomic environments and corresponding shorthand codes of the form [WXY/Z] are listed in Table 1 (FIG. 7). The atomic ESVD environments listed in Table 1 are illustrated in FIG. 8, in which dashed bonds represent the fixed bonds that are replacing delocalized bonds.

Table 1 is not a complete list, but furnishes the essential elements and values for at least some cases. With respect to the external bonds column, if an atom has a third delocalized bond, an "external bond" is appropriated to represent it. With respect to the text "like N" in the first entry for element P, a "treat-like" element (such as P) inherits all of the entries for its parent (such as N in the case of P) and may have additional unique entries.

All possible ESVDs may be attempted for all atoms, and all bond orders (including single and double) may be attempted for all bonds. A solution is determined to have been found when a combination of codes and orders is self-consistent, such that, for every atom, the orders of bonds to the atom match the requirements of the atom's ESVD, and the net charge and number of paired electrons of the system are also as required by the structure. Possible further requirements include a satisfactory 4n+2 electron count or an absence of radicals or zwitterions.

In a specific implementation, the procedure includes several practical features that help to produce timely results in practice. A first of the practical features reflects a recognition that it is not always necessary to try all ESVDs and bond orders: with respect to choosing an order for a bond to an atom having an assigned ESVD, the only orders considered are orders that are consistent with the ESVD, taking account of bonds already assigned. For example, if a carbon ([121/1]) has been assigned a double bond, the carbon's next bond may not be double, and is only considered to be single. Further, the only ESVDS that are chosen are ESVDs that are consistent with adjacent fixed bonds.

A second of the practical features is consistent with a recognition that in practice many or most solutions do not involve unpaired electrons or charge: ESVDs featuring unpaired electrons or charge are not considered initially. If a solution is found without referring to such ESVDs, the procedure is finished, and time has been saved.

According to a third of the practical features, the procedure is only partially recursive. With respect to bond orders, when alternative bond orders are attempted, recursion is sensible: if a single bond appears to be the most advantageous next step, and its recursive development returns in failure, the double bond remains the most advantageous next option. In other words, pursuit of a bond order is exhaustive. By contrast, with respect to ESVDs, some ESVDs tend to be more promising (i.e., better) than others, in at least some cases. Accordingly, after the possible ESVDs for an atom are tabulated, the best of the possible ESVDs is actually pursued, recursively, and the rest of the possible ESVDs are placed in a priority queue, keyed to a rating of the inchoate structure's likelihood of success. In this way, less promising ESVDs are not examined until more promising combinations are exhaustively considered.

Another of the practical features in a computer-based implementation is an implementational measure that speeds the assessment of compatibility between bonds and ESVDs: a screening bitmask. (A bitset is a piece of data, e.g., an integer, in which each bit represents a Boolean value. As used herein, a bitmask is synonymous with a bitset.) For a given ESVD, a screening bitmask encodes the ESVD's bonding and electron requirements. Similarly, for an atom, another screening bitmask specifies which types of bond have already been fixed. When the latter screening bitmask is logically (i.e., bitwise) subtracted from the former screening bitmask, a list of bond types still required at the atom is obtained. By logically subtracting the former screening bitmask from the latter screening bitmask, it can be determined whether it is possible to apply the ESVD to the atom. Such operations tend to save time, since multiple logical comparisons are compressed into one comparison of bitmasks.

In a specific implementation, the screening bitmask for the ESVD [121], for example, can be figured from Table 3 (FIG. 11). Only the bonding portion of the bitmask is considered when choosing the bond orders compatible with an ESVD. The internal single bond, the internal double bond, and the external single bond of the ESVD [121] correspond to bits #0, #2, and #4, respectively. Therefore, the bitmask has the value {0,2,4}. For an atom that has had one single bond fixed, the bitmask consists of bit #0, with the value {0}. The difference between the former and latter bitmasks, {0,2,4}–{0}={2,4}, reveals the fixed bond types that must eventually be assigned to the atom, namely, an internal double bond (bit #2 and an external single bond (bit #4).

An example of the opposite process is determining whether an ESVD, such as [111/2–], is compatible with an atom that, for example, has two fixed single bonds and which, due to a global restraint, may not be charged. The ESVD's bitmask is {0,1,4,10,12,14}, indicating that the ESVD has an internal single bond, has two internal single bonds, has an external bond, is negative, is not positive, and does not have an unpaired electron, respectively. The atom's bitmask is {0,1, 8,11,12}, indicating the atom has an internal single bond, has two internal single bonds, is neutral, is not an anion, and is not a cation, respectively. The atom's bitmask {0,1,8,11,12} is not a subset of the ESVD's bitmask {0,1,4,10,12,14}, which indicates that the ESVD is not compatible with the atom. Although the bonding portions are compatible, the electronic portions are not. (In general, the more fully characterized or developed an atom is, the more bits are set in its bitmask, and the less likely that the atom will be compatible with a given ESVD.)

Different applications of the dekekulization procedure may have slightly different requirements. Thus, in at least some cases, it may be advantageous for the procedure to refer to a bitset of control flags, listed in Table 2 (FIG. 9).

Figure 10:
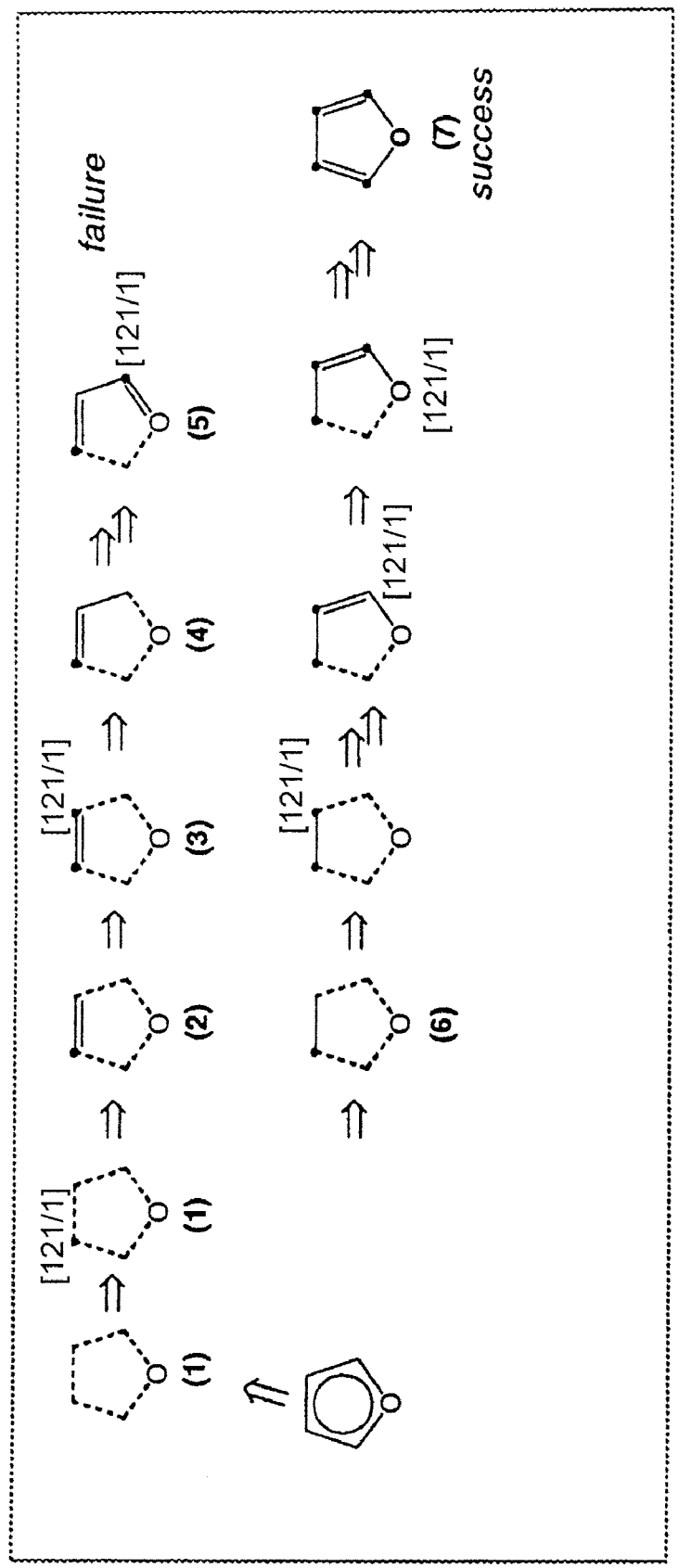
Figure 22:
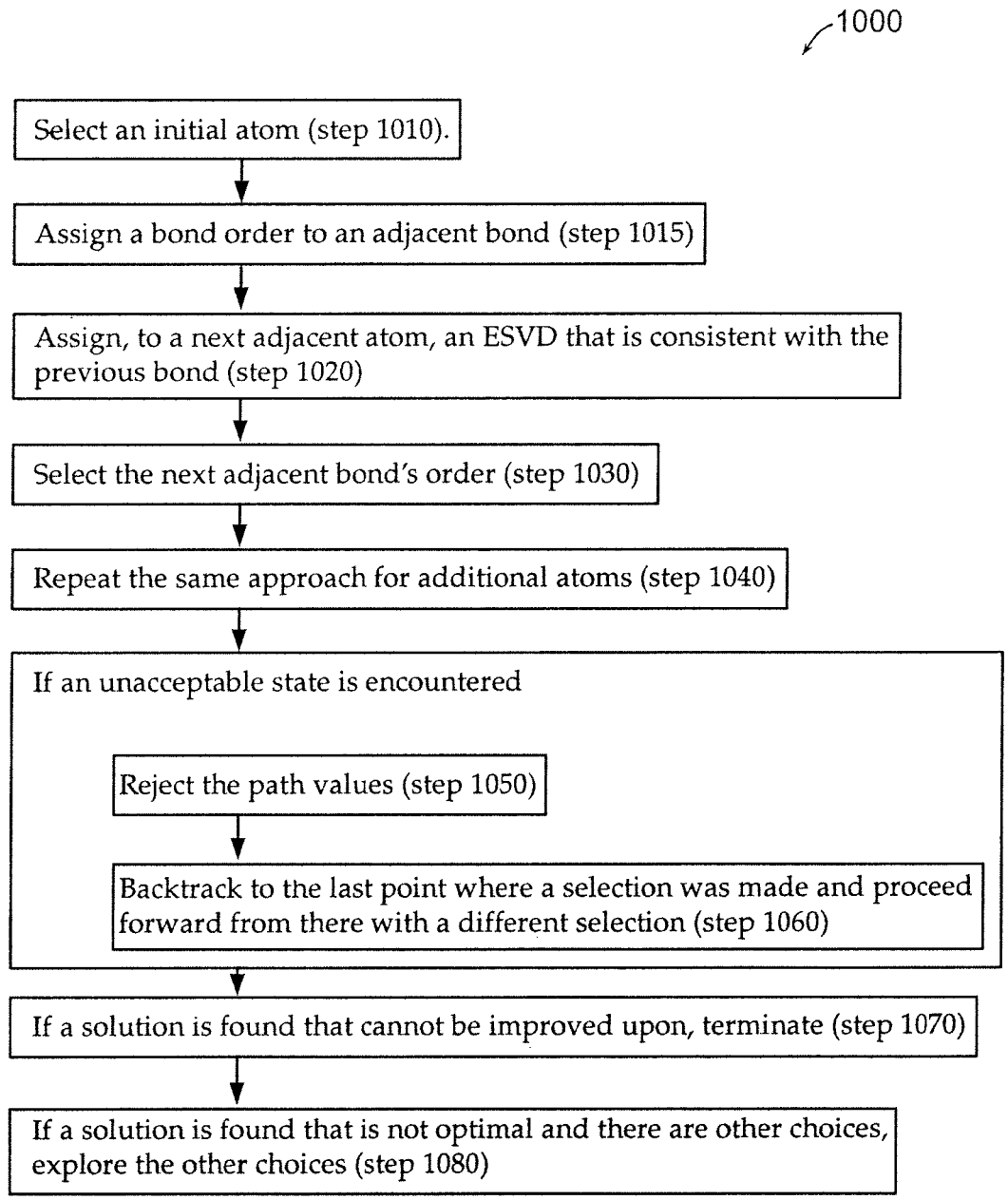

An example 1000 of the procedure is illustrated generally in FIGS. 10, 22 and is now discussed generally; a more detailed example is included below. FIG. 10 illustrates an example of environment development and backtracking for furan. In this particular example, for simplicity, solutions that incorporate charges or unpaired electrons are not considered. Initially, none of the atoms or bonds has been assigned. An initial atom is selected (step 1010). For example, the top left atom is arbitrarily selected and is assigned the only neutral and non-radical environment for carbons that is also free of external pi bonding: [121/1] (see FIG. 6). Thus the top left atom will have a single and a double bond disposed within the originally delocalized system, and a single bond disposed without. The top left atom contributes one pi electron to the delocalized system.

A bond order is assigned to an adjacent bond (step 1015). Either a single bond order or a double bond order may be selected. In this case, a double bond order is arbitrarily chosen at this point. As explained below, after the ramifications of the double bond order choice have been extensively or exhaustively explored, the procedure returns to this point and proceeds with the single bond order choice instead.

A next adjacent atom is assigned an ESVD that is consistent with the previous bond, here, the double bond (step 1020). Since the example includes no ions or radicals, the ESVD that is assigned is [121/1].

The next adjacent bond's order is selected (step 1030). Since the preceding atom has a double bond, the only choice for the order that is consistent with the atom's environment is a single bond.

The same approach is repeated for additional atoms (step 1040).

If an unacceptable state is encountered, the path values are rejected (step 1050). In this case, a state is encountered in which the oxygen atom has one double bond and one uncharacterized bond. Since no (ESVD) type of uncharged oxygen can accommodate this state, the state is unacceptable and the path values are rejected.

The procedure backtracks to the last point where a selection was made, and proceeds forward from there with a different selection (step 1060). In this example, the procedure proceeds forward with the single bond order choice as noted above.

If a solution is found that cannot be improved upon, i.e., if all atoms and bonds have been assigned mutually compatible environments and orders, respectively, and the collection is holistically optimal, the procedure terminates (step 1070). On the other hand, if a solution is found that is not optimal and there are other choices, such as were encountered with respect to the alternative bond order choices above, the other choices are explored (step 1080). The principal factors in the holistic value of the solution are the count of the delocalized electrons in each ring, and whether an excessive number of charges or radicals or both are present.

A more detailed example of the procedure is now described, with the use of terms as now explained. A "delocalized atom" is an atom having a vacant pi orbital that is shared, or one or more pi electrons that are shared, with one or more adjacent atoms. (The term pi is intended to encompass d and f orbitals and any other orbitals that participate in delocalized bonding.) A bond that holds the one or more shared pi electrons is called a "delocalized bond", and in the delocalized style of depiction is drawn as a single bond with a nearby arc or circle.

The largest set of contiguous delocalized bonds containing a given delocalized bond is called a "delocalized system". The atoms in the delocalized system are those adjacent to the delocalized bonds. As a result, an atom or bond may belong to at most one delocalized system. Contributions emanating from inside and outside the delocalized system are "internal" and "external", respectively. For example, sigma bonds and exo double bonds are external.

The "internal coordination number" ("ICN") of a delocalized atom is the count of its adjacent atoms that belong to the same delocalized system. Although only ICNs from 1 to 3 are described herein, the concepts involved are extensible to larger ICNs.

A delocalized atom's "internal order" is its bond order sum, after bond fixation, contributed by formerly delocalized bonds, and cannot be determined before bond fixation. A delocalized atom's "external" order is the bond order sum emanating from outside the delocalized system, and is known from the outset unless implicit hydrogen atoms are in question.

Each element is associated with a respective list of electronic state and valence distribution ("ESVD") values that are available (see Table 1 in FIG. 7). An ESVD specifies the number of bonds to an atom, their orders, and the charge and radical state of the atom. Separate accounting is made for internal and external bonds. Additionally, a distinction may be made between an external multiple bond and a set of several external bonds of lower order, where the sum of the bond orders in the set equals the order of the external multiple bond. A solution is found when mutually consistent ESVDS (i.e., with correct bonding) have been found for all atoms, and the net charge and radical count are correct for the system.

Figure 29:
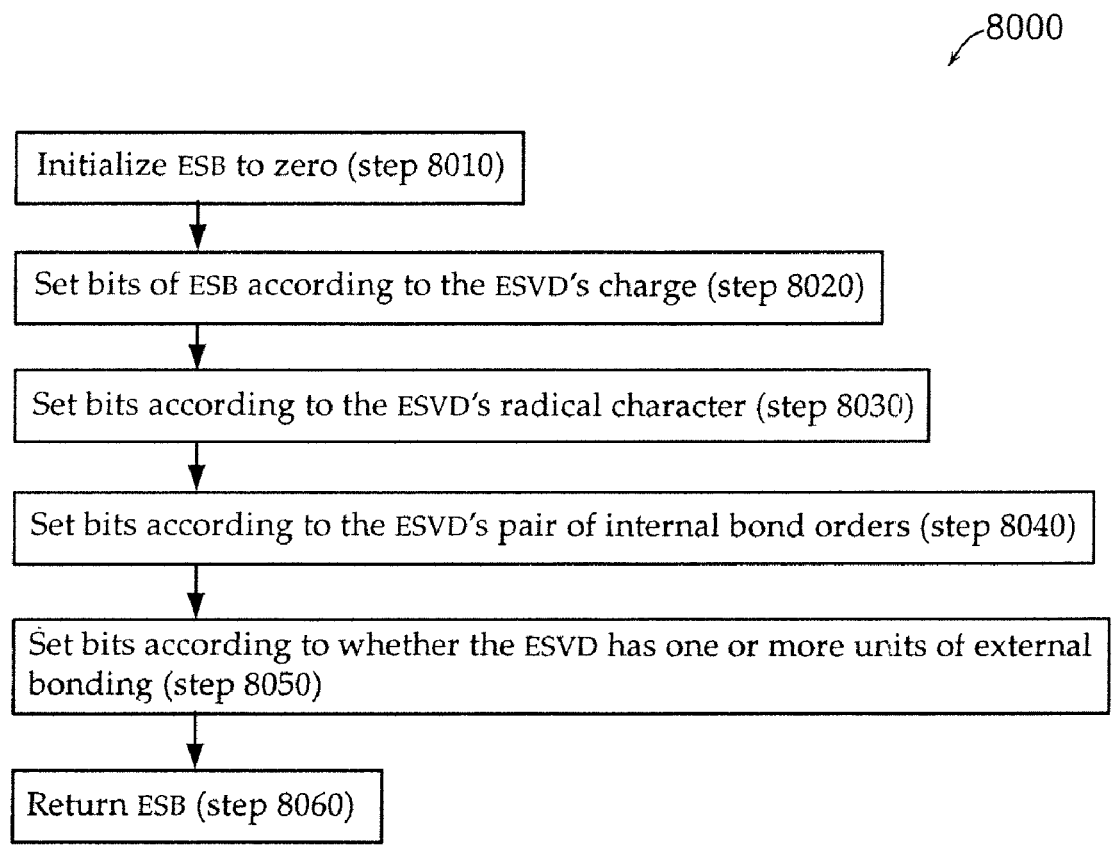

An ESVD screening bitmask ("ESB") is used to determine whether a given ESVD is compatible with a given atom. The ESB is a constant for a given ESVD, and is computed from the corresponding ESVD at run time (see procedure 8000 in FIG. 29, discussed below). The ESB is a bitset (i.e., a bitmask), which is a binary number, each bit of which represents a Boolean value indicating whether a condition is present or absent. Table 3 (FIG. 11) illustrates the meanings of the bits in the ESB.

Figure 30:
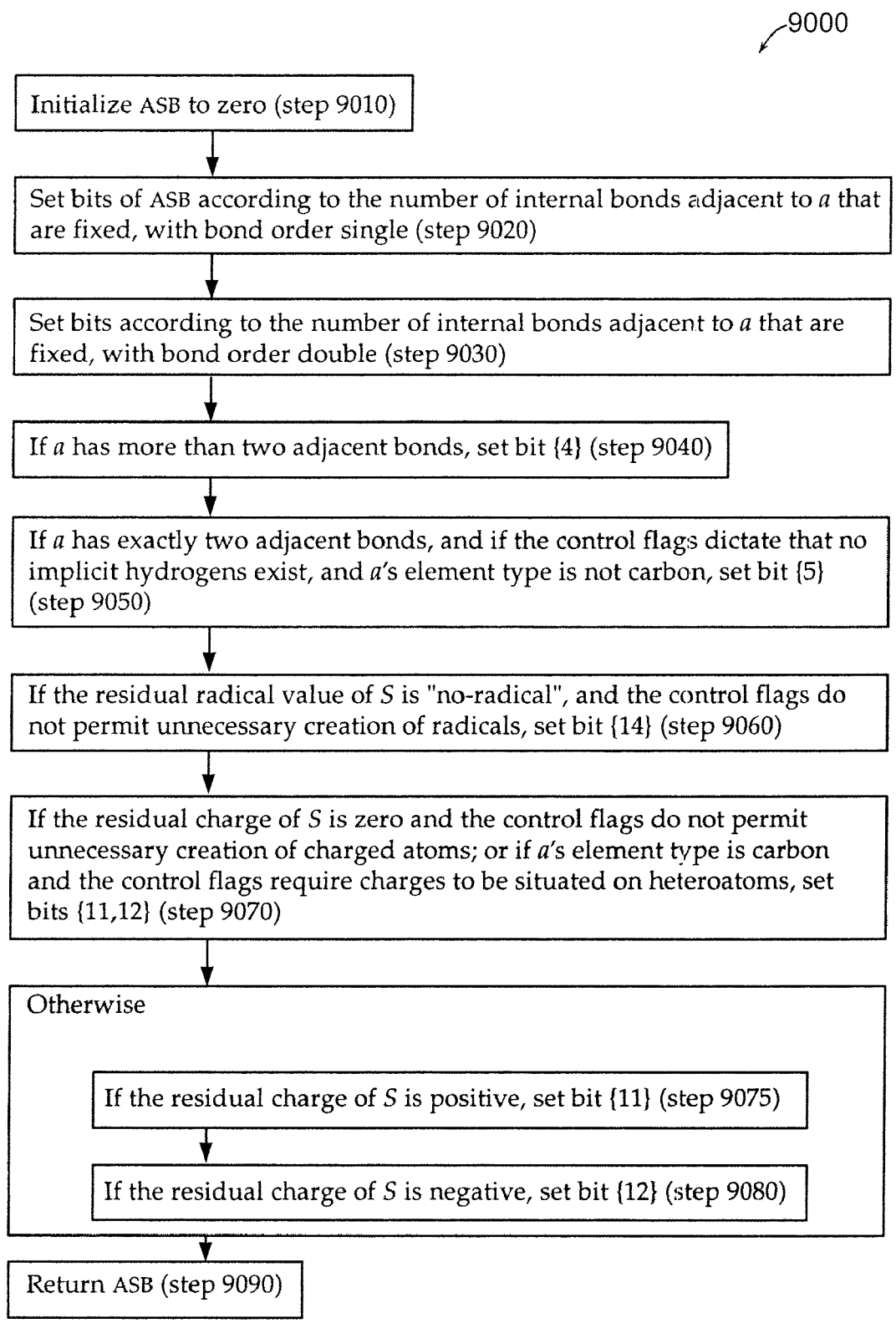

An atom screening bitmask ("ASB") has the same bit values as the ESB (Table 3, FIG. 11), but is computed slightly differently (see procedure 9000 in FIG. 30, discussed below). An ESVD can be assigned to a given atom if the atom's ASB is a subset of the ESVD's ESB.

Figure 12:
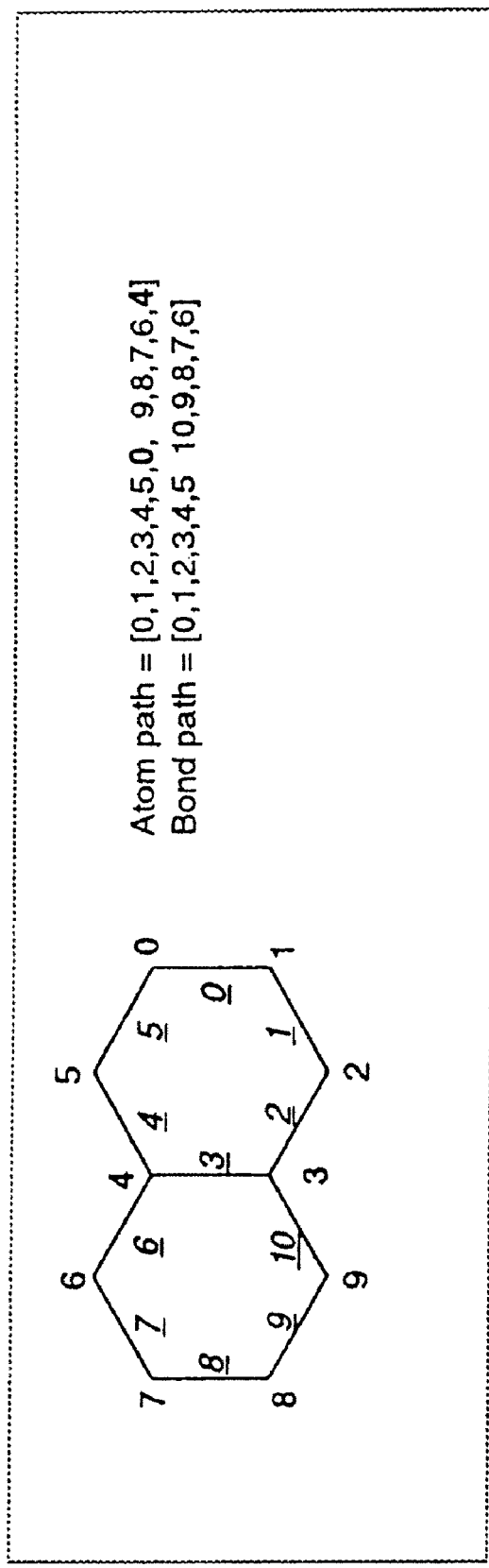

A "path" taken through a system (cyclic or not) is a type of directed graph, and is represented by a vector of atom and bond numbers, in the order in which the atoms and bonds will be considered. FIG. 12 illustrates an example of a path, marked with atom and bond (underlined) numbers, in which ring closure atoms appear in bold; the path may be discontinuous. It is not necessary for consecutive path bonds to be adjacent, as long as every later-occurring bond is adjacent to any of the earlier-occurring bonds.

A "strategy" for the system is a script that drives path development, and is formulated at the same time the path is created. Various actions possible in a step of the script are shown in Table 4 (FIG. 14). The strategy for the example of FIG. 12 is shown in FIG. 13.

A "state" is a data structure that includes the information about the choices made in the path up to the current point, and refers to a "residual charge", a "residual radical", and a "strategy step index", as well as the ESVD and bond order assignments. A residual charge is the amount of charge remaining to be dispelled by a suitable choice of charged atoms. For example, a residual charge of +2 requires that two cations, or three cations and an anion, or other ion set that adds up to a +2 charge, be chosen in the course of the rest of the path. A residual radical can be zero ("no-radical") or one ("radical"). If the residual radical is one, an odd number of radicals must be assigned in the course of the rest of the path. If the residual radical is zero, an even number must be so assigned. A strategy step index notes the most recent step number executed in the strategy list.

In at least some cases, one or more of the features presented may be advantageous but not essential. For example, the pre-identification of the path and the use of a strategy script based on the path, are logical simplifications; instead of iterating over the script's steps, the part of the procedure that assigns a bond order or an ESVD may directly invoke the next logically succeeding step. In at least some computer-based implementations, maintenance of the strategy involves processing overhead that is not insignificant, but that also contributes logical order and stability. Similarly, the use of an ESB or an ASB may be an implementational convenience that is not essential. Note that all quantitative values cited herein are provided for illustrative purposes only, and are not necessarily optimal for any or all cases.

Figure 23B:
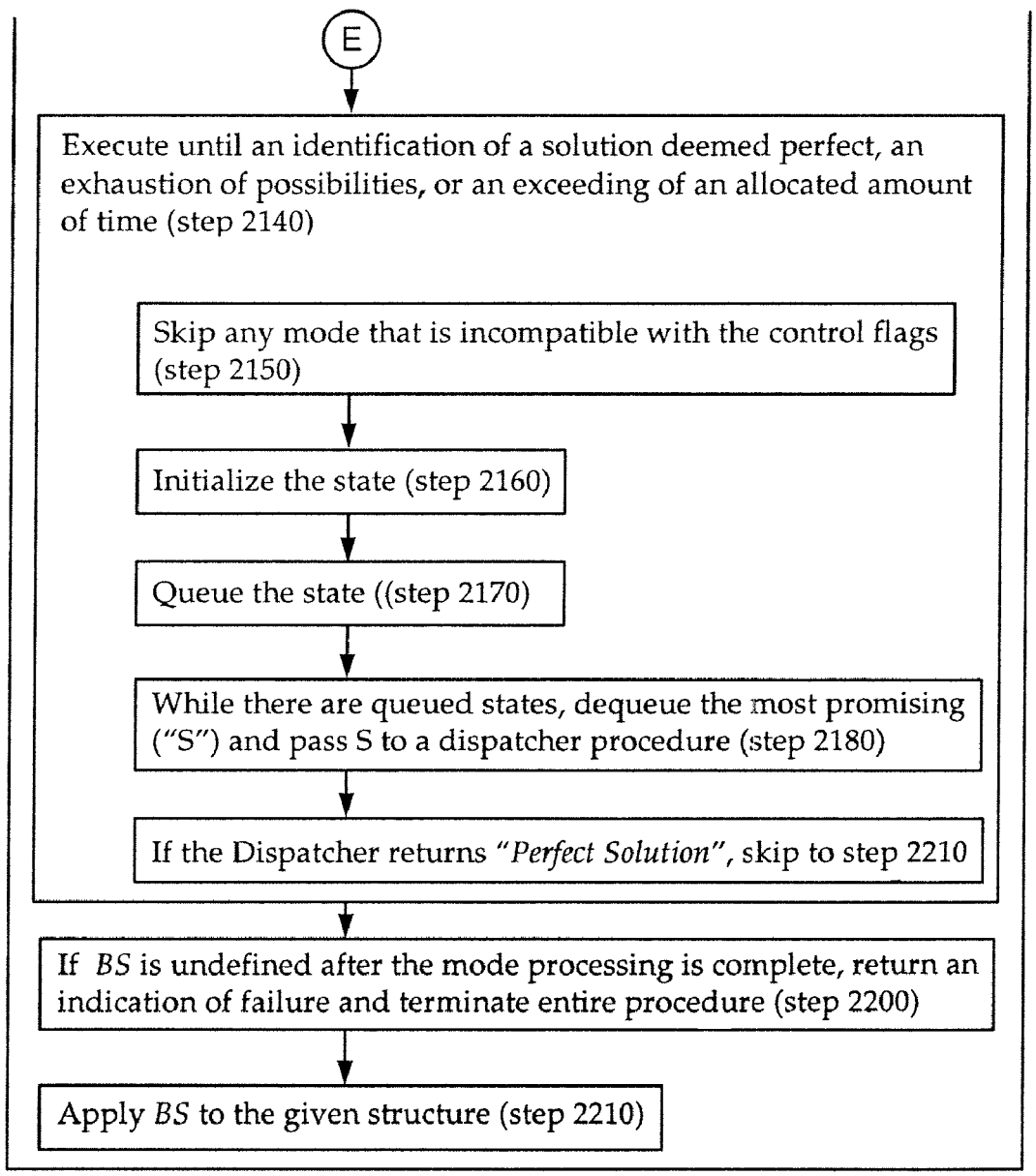

In an example implementation, the dekekulization procedure includes a procedure 2000 (FIGS. 23A-23B), now described, that is provided with information describing a chemical structure, an indication of which of the structure's bonds are of interest, a bitmask of control flags, and an indication of a timeout period. In at least some cases, the bonds of interest include the complete set spanning the structure. The procedure ignores non-delocalized bonds. The bitmask of control flags is as described above (Table 2 in FIG. 9). The timeout period is the interval after which the procedure should terminate and present its best solution, even if that solution is imperfect. In a specific implementation, the timeout period is more than sufficient in a typical case, for which the production of the fully satisfactory solution is nearly instantaneous. Procedure 2000 returns an indication of success or failure, depending on whether bonds have been successfully fixed.

In procedure 2000, discrete (i.e., not adjacent) delocalized systems present in the structure are identified (step 2010). (As used herein, "structure" refers to a collection of one or more molecules, and an ion qualifies as a molecule.) Each next system is identified by selecting any delocalized bond that has not already been treated (step 2020), adding all adjacent delocalized bonds (step 2030), and continuing to add delocalized bonds adjacent to those just found, until no new bonds are added (step 2040).

Steps 2060-2120, now described, are executed for each of the identified delocalized systems (step 2050). The instant delocalized system is denoted "DS". DS is analyzed for characteristics (step 2060). In a specific implementation, the analysis proceeds as follows. The total charge and radical count required of the pi system are noted (step 2070). (Charges localized in sigma orbitals, such as in phenyl lithium, are not included, and are ignored throughout procedure 2000.) The internal coordination number ("ICN") of each atom is calculated (step 2080). Bonds in DS are identified that must be fixed, as a consequence of having an adjacent fixed multiple bond (step 2090). (This is limited to carbon atoms if there is ambiguity in the valence of polyvalent elements.)

A path through DS is developed (step 2100). In at least some cases, it does not matter substantially whether the path is breadth-first, depth-first, or is of some other type. However, it has been found in some cases that highly efficient paths tend to be those that complete rings promptly. The path need not be continuous, although every path atom (bond) other than the first must be adjacent to one previously visited. If any fixed bonds were identified in step 2090, the process begins with an adjacent atom, which tends to limit the choices for the succeeding bond order. (In general, in at least some cases, it is advantageous to defer choices in state and bonding to as late in the path as possible.)

The strategy list is constructed (step 2110). The strategy list includes directives to assign ESVDs and bond orders for the atoms and bonds encountered in the path, and additionally directives to check each atom's final environment the last time the atom is visited.

Ring systems are identified (step 2120). A ring system is a group of one or more rings, each of which shares one or more bonds with another in the group, that cannot be divided into two or more smaller ring systems without breaking a ring bond. As used herein, "ring" refers only to a cycle that contains one or more delocalized bonds, or that is adjacent to such a cycle. Other cycles are ignored.

The best solution ("BS") is set to "undefined" (step 2130).

For each of three modes, now described, steps 2150-2190 described below are executed for as long as they do not terminate, either as a result of an identification of a solution deemed perfect, or by exhausting possibilities, and the time elapsed does not exceed an allocated amount of time (step 2140). Any mode that is incompatible with the control flags is skipped (step 2150). According to mode 1, charges or radicals beyond those provided are not created, and any charges (and optionally radicals) are confined to heteroatoms. In the case of mode 2, charges and radicals are handled in the same way as in mode 1, except that there is no restriction on their placement. In mode 3, radicals and charges are freely created, without restriction on their placement.

The state is initialized (step 2160) as follows. The state's charge count is set to that of the system. If the system has an odd number of unpaired electrons, the residual radical flag is set; otherwise it is cleared. The state's strategy step index is set to zero, indicating a point immediately preceding the first step in the strategy.

The state is queued (the queue is effectively empty at this point) (step 2170).

While there are queued states, the most promising ("S") is dequeued and is passed to a dispatcher procedure ("Dispatcher", described below), (step 2180). If the Dispatcher returns "Perfect Solution", the procedure skips to step 2210.

If BS is undefined after the mode processing is complete, an indication of failure is returned, and the entire procedure terminates (step 2200).

BS is applied to the given structure (step 2210), so that bond orders are fixed and charges and radical values are assigned to atoms as required by BS. (Where identification of implicit hydrogens is of interest, these are determined from the ESVDs of the heteroatoms. That is, if the valence of a heteroatom's ESVD is larger than the its apparent valence after bond fixation, the difference is made up with hydrogen atoms. The entire procedure terminates, returning a value of success.)

Figure 24:
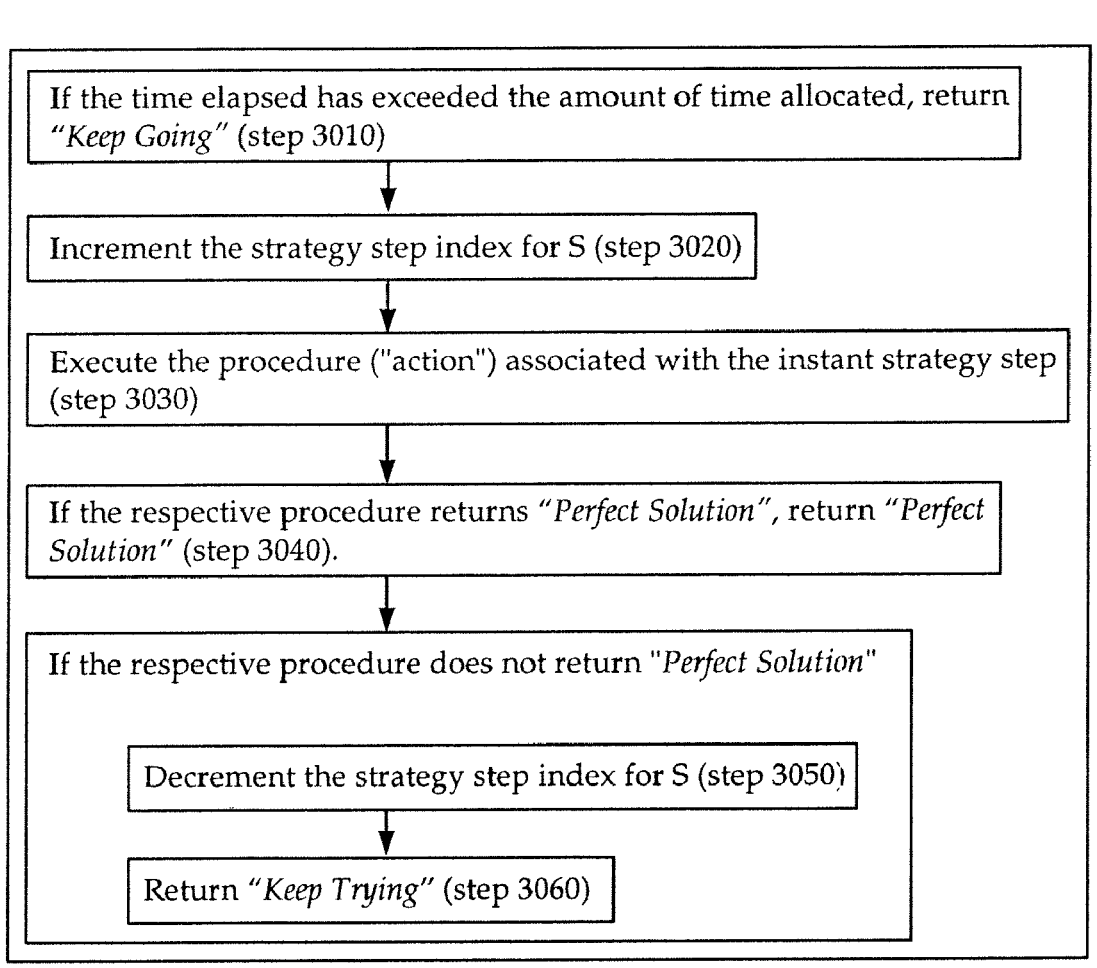

The Dispatcher executes as follows when provided with a state ("S"). In general, the Dispatcher recursively executes the next strategy step and returns either "Perfect Solution" or "Keep Trying". In a specific implementation, the following steps are executed (procedure 3000, FIG. 24). If the time elapsed has exceeded the amount of time allocated, "Keep Going" is returned (step 3010). Otherwise, the strategy step index for S is incremented (step 3020), and the Dispatcher continues as follows. The procedure ("action") associated with the instant strategy step is executed (see Table 4 in FIG. 14), as indicated below (step 3030), and if the respective procedure returns "Perfect Solution", the Dispatcher returns "Perfect Solution" (step 3040). Procedures 4000-7000 are described below.

| | |
|---|---|
| Assign ESVD: | Execute procedure 4000. |
| Assign Bond: | Execute procedure 5000. |
| Verify Completed: | Execute procedure 6000. |
| Complete: | Execute procedure 7000. |

If the respective procedure does not return "Perfect Solution", the strategy step index for S is decremented (step 3050), and "Keep Trying" is returned (step 3060).

Figure 25A:
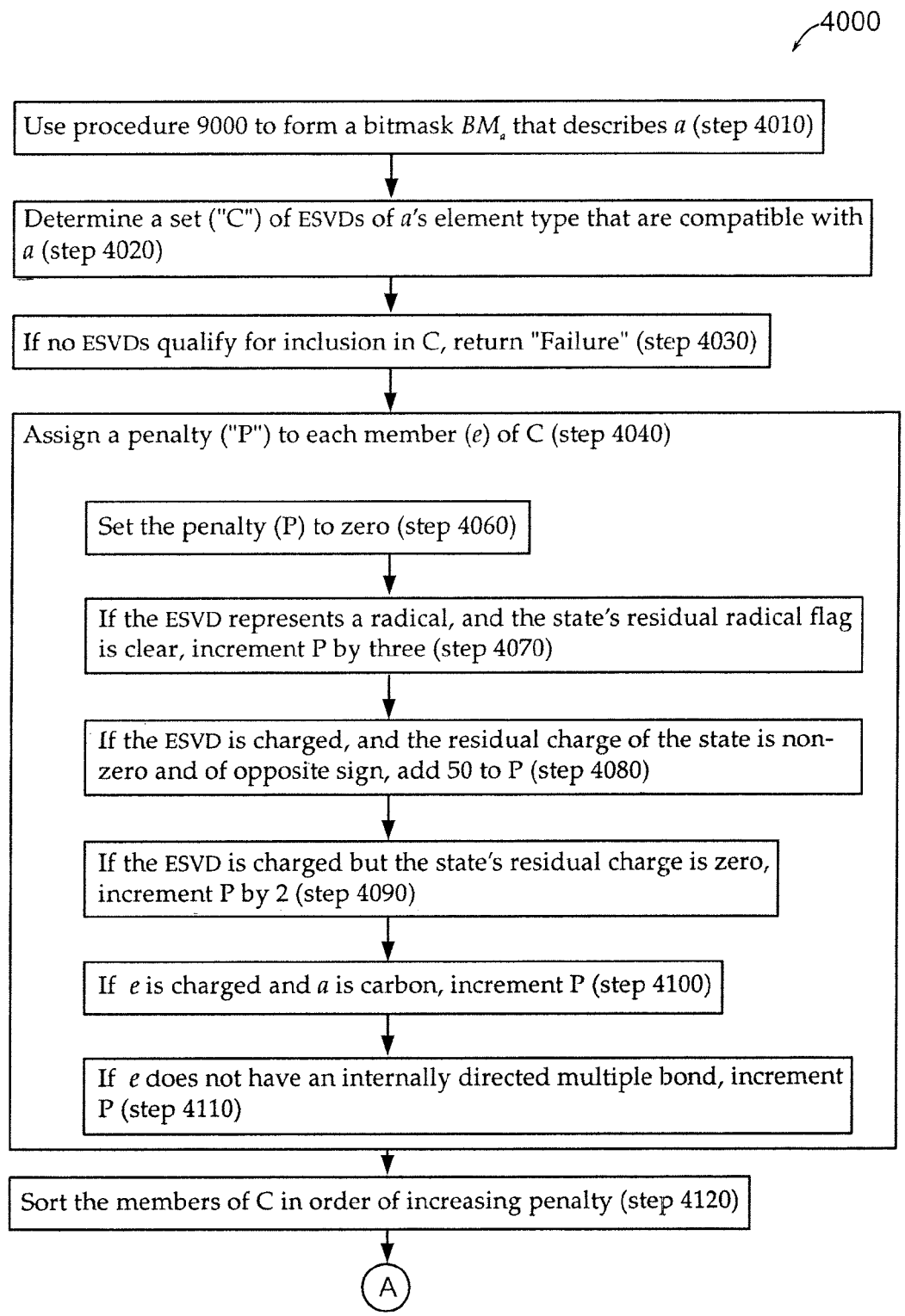
Figure 25B:
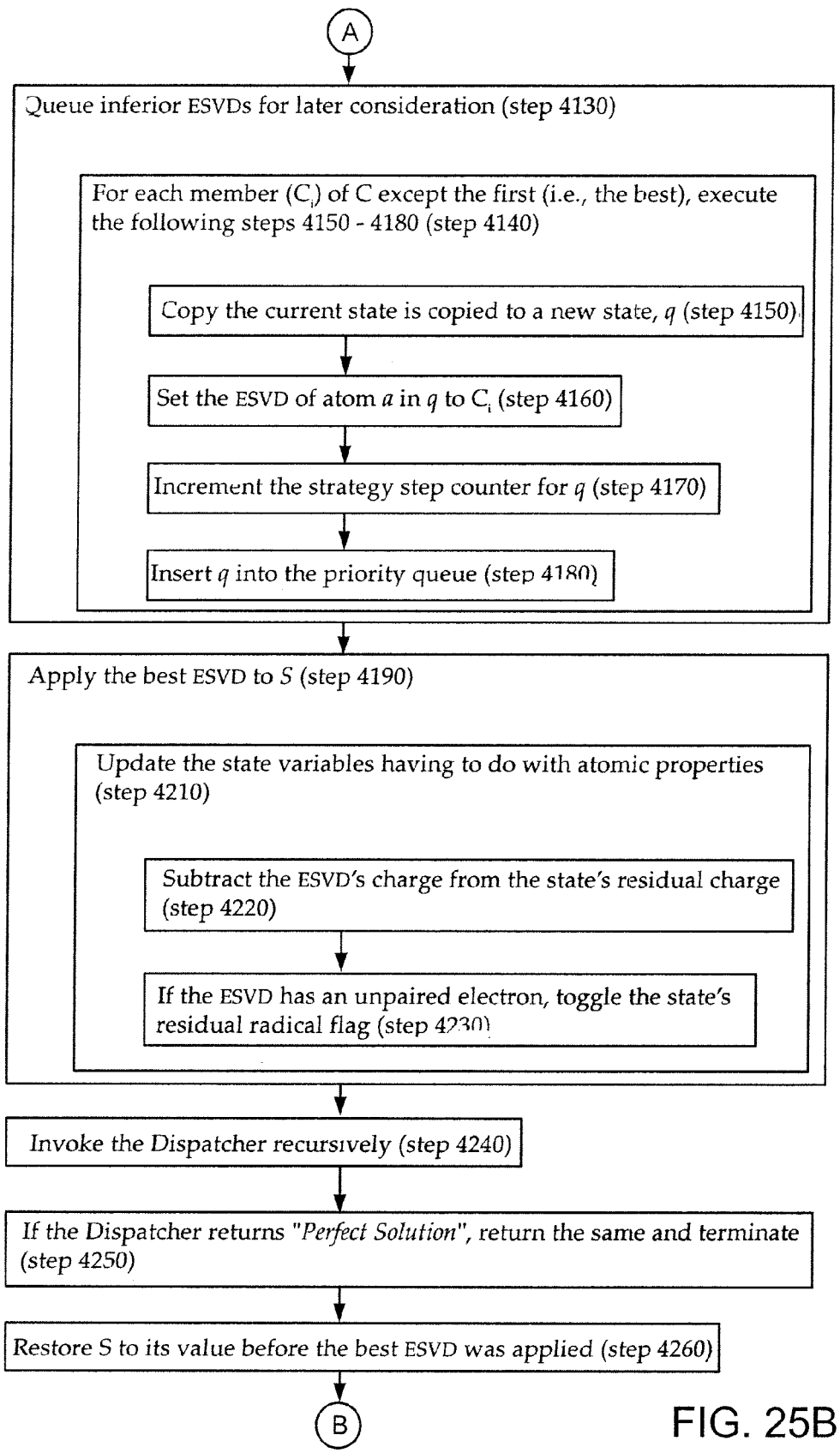
Figure 25C:
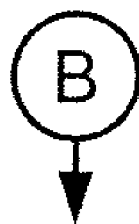

In procedure 4000 (FIGS. 25A-25C), an ESVD is assigned. Generally, procedure 4000 is provided with the state ("S"), as so far developed, and an atom ("a") to be assigned an ESVD, and returns either "Perfect Solution" or "Keep Trying". Zero or more of a's bonds have been fixed at this point. In a specific implementation, the following steps are executed.

A bitmask $BM_a$ that describes a is formed using procedure 9000 (FIG. 30) (step 4010) For each of a's fixed bonds, the bit is set in $BM_a$ corresponding to its bond order (see Table 3 in FIG. 11). If a has an external bond, the corresponding bit is set in $BM_a$. If the operative mode does not permit spontaneous generation of radicals, the no-radical bit is set. If the operative mode does not permit creation of charges, the no-plus and no-minus bits are set.

The ESVDS available to a include all of the element's ESVDS that contain, bitwise, all of the bits present in $Bm_a$.

A set ("C") is determined of ESVDS of a's element type that are compatible with a (step 4020). An ESVD is determined to be compatible if the ESVD has an ESB that is a superset of $BM_a$. If no ESVDS qualify for inclusion in C, "Failure" is returned (step 4030).

A penalty ("P") is assigned to each member (e) of C (step 4040). The penalty represents an assessment of the strategic desirability of using the ESVD. The penalty value is zero or positive, with larger values corresponding to lower desirability. In a specific implementation, each penalty is calculated as follows (steps 4050-4110). Initially, the penalty (P) is set to zero (step 4060). If the ESVD represents a radical, and the state's residual radical flag is clear, P is incremented by three (step 4070). If the ESVD is charged, and the residual charge of the state is non-zero and of opposite sign, 50 is added to P, thus practically eliminating the ESVD from consideration (step 4080). If the ESVD is charged but the state's residual charge is zero, P is incremented by 2 (step 4090). If e (i.e., the ESVD) is charged and a is carbon, P is incremented (step 4100). If e does not have an internally directed multiple bond, P is incremented (step 4110).

At this point, each penalty has been calculated. The members of C are sorted in order of increasing penalty (step 4120).

Inferior ESVDS are queued for later consideration (step 4130). In a specific implementation, the queuing proceeds as follows (steps 4140-4180). For each member ($C_i$) of C except the first (i.e., the best), the following steps 4150-4180 are executed (step 4140). The current state is copied to a new state, q (step 4150). The ESVD of atom a in q is set to $C_i$ (step 4160). The strategy step counter for q is incremented, so that when the state is dequeued, state development will resume after a's ESVD assignment (step 4170). Further, q is inserted into the priority queue, and is ranked therein based on the penalty respectively assigned as described above (step 4180). (In a case in which the queue has a finite capacity, the worst entry is deleted to make room for the new one.)

At this point, the inferior ESVDS have been queued. The best ESVD is applied to S (step 4190). In a specific implementation, the application is executed as follows (steps 4200-4230). The state variables having to do with atomic properties are updated (step 4210): the ESVD's charge is subtracted from the state's residual charge (step 4220), and if the ESVD has an unpaired electron, the state's residual radical flag is toggled (step 4230).

The Dispatcher (i.e., procedure 3000) is recursively invoked (step 4240), and if the Dispatcher returns "Perfect Solution", the instant procedure returns the same (step 4250).

Otherwise, S is restored to its value before the best ESVD was applied (step 4260), and "Keep Trying" is returned (step 4270).

Figure 26A:
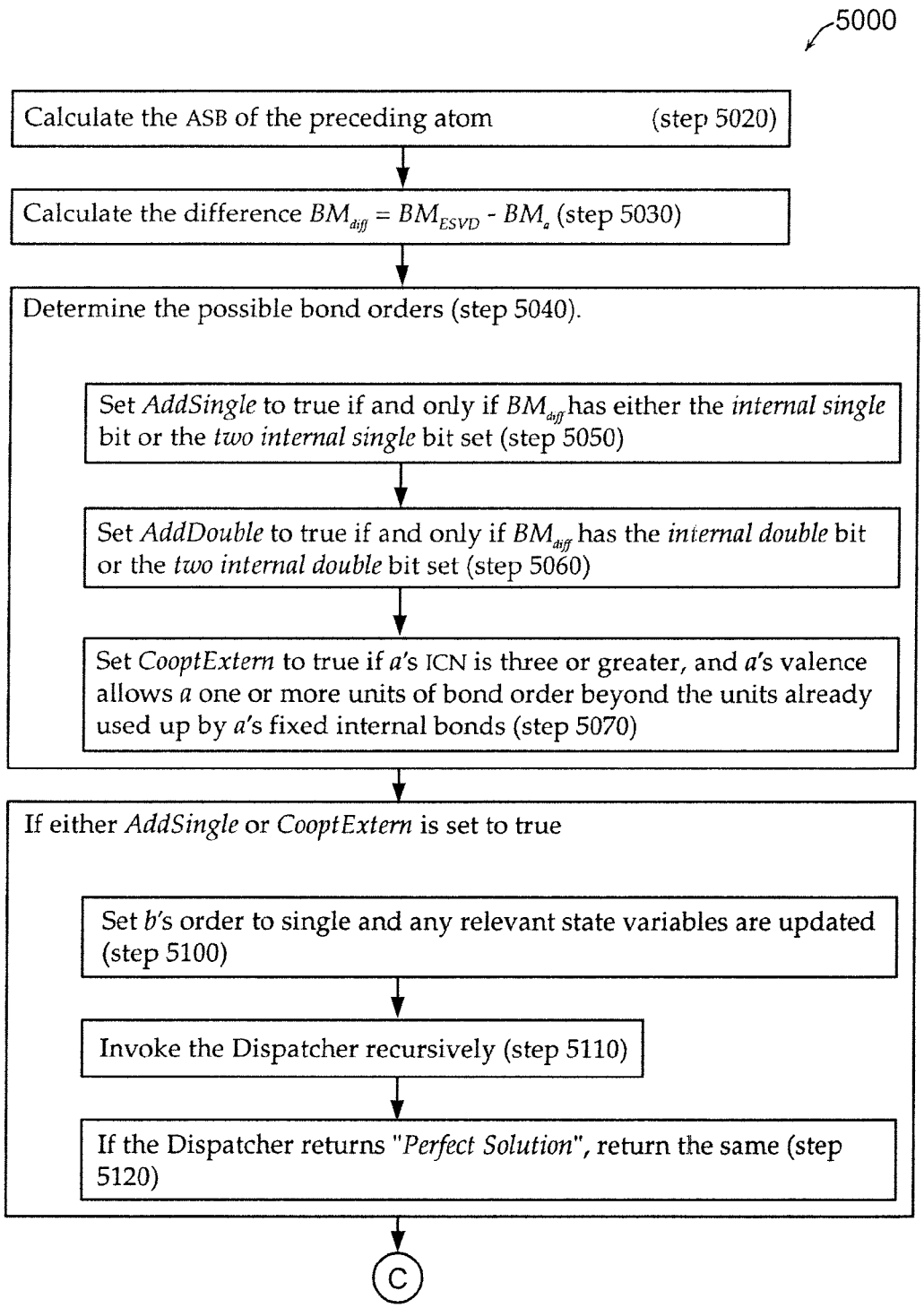
Figure 26B:
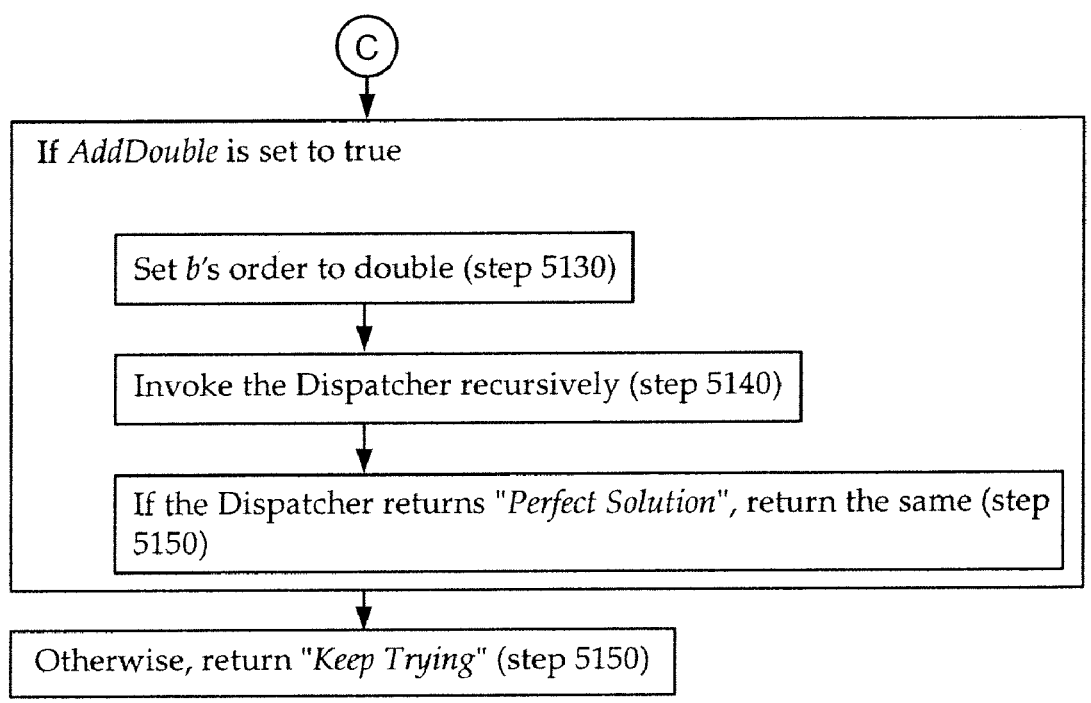

In procedure 5000 (FIGS. 26A-26B), a bond order is assigned. Procedure 5000 is provided with the current state ("S"), the bond to be fixed ("b"), and the atom ("a") preceding this bond in the path, and returns "Perfect Solution" or "Keep Trying". In a specific implementation, the bond order is assigned as follows (steps 5020-5150). The ASB of the preceding atom is calculated (step 5020) and is called $BM_a$. $BM_{esvd}$ is the ESB of a's ESVD.

The difference $BM_{diff}=BM_{ESVD}-BM_a$ is calculated (step 5030). Only the bond-order bits (0-5 of Table 3 of FIG. 11) are of interest. The presence of a given bond-order bit in $BM_{diff}$ indicates the particular option is available.

The possible bond orders are determined (step 5040). In a specific implementation, the determination proceeds as follows (steps 5050-5150). AddSingle is set to true if and only if $BM_{diff}$ has either the internal single bit or the two internal single bit set (step 5050). AddDouble is set to true if and only if $BM_{diff}$ has the internal double bit or the two internal double bit set (step 5060). CooptExtern is set to true if a's ICN is three or greater, and a's valence allows a one or more units of bond order beyond the units already used up by a's fixed internal bonds (step 5070).

Figure 15:
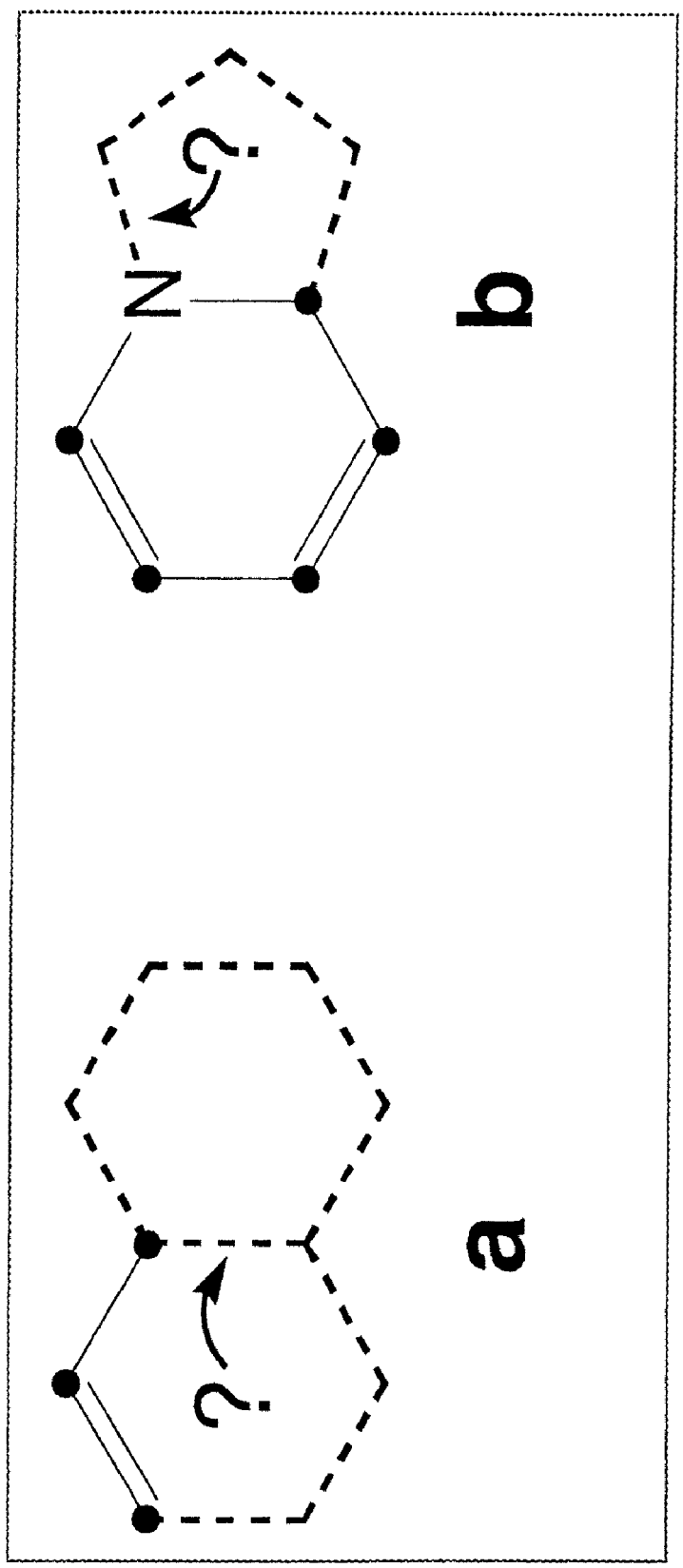
Figure 16:
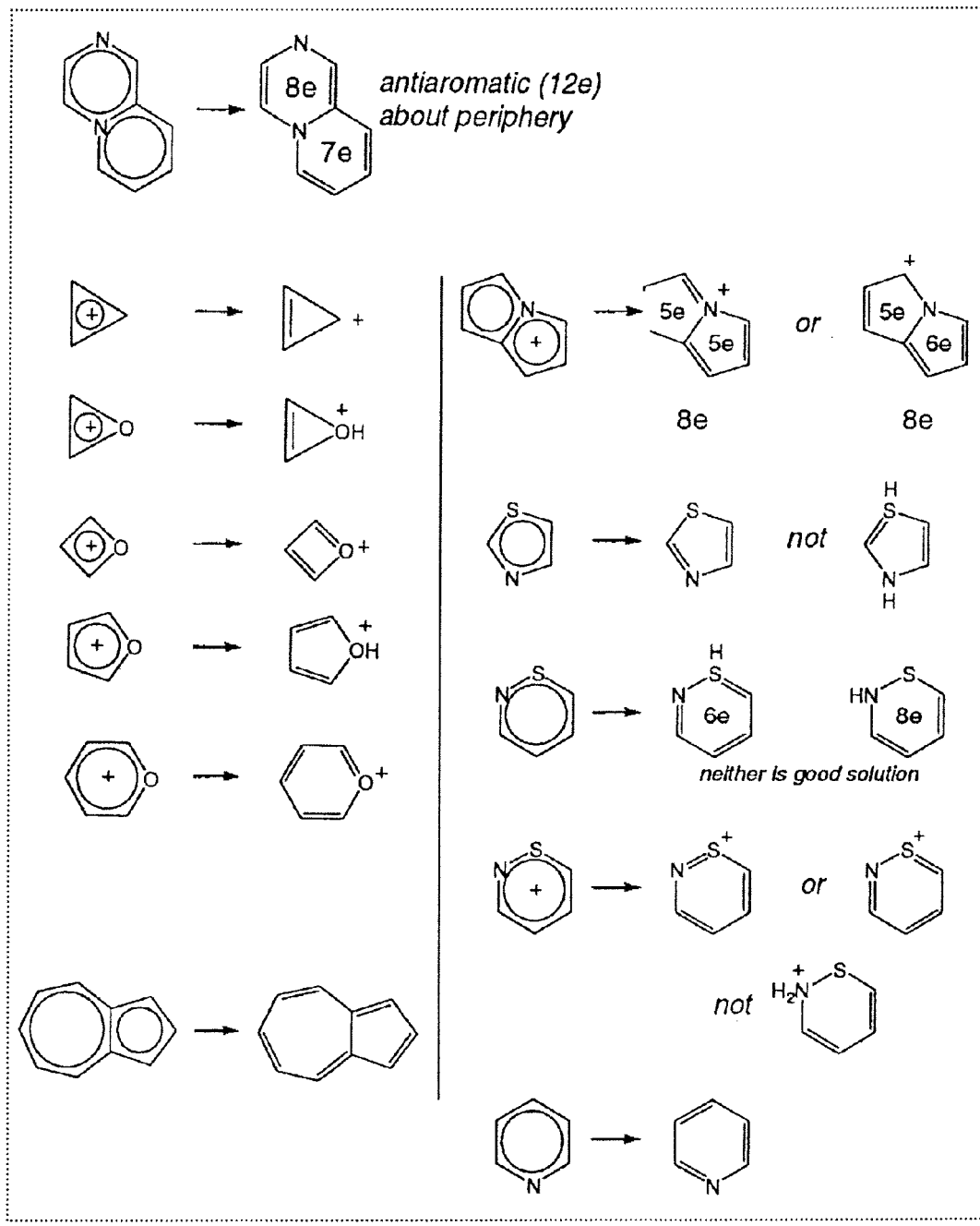
Figure 18:
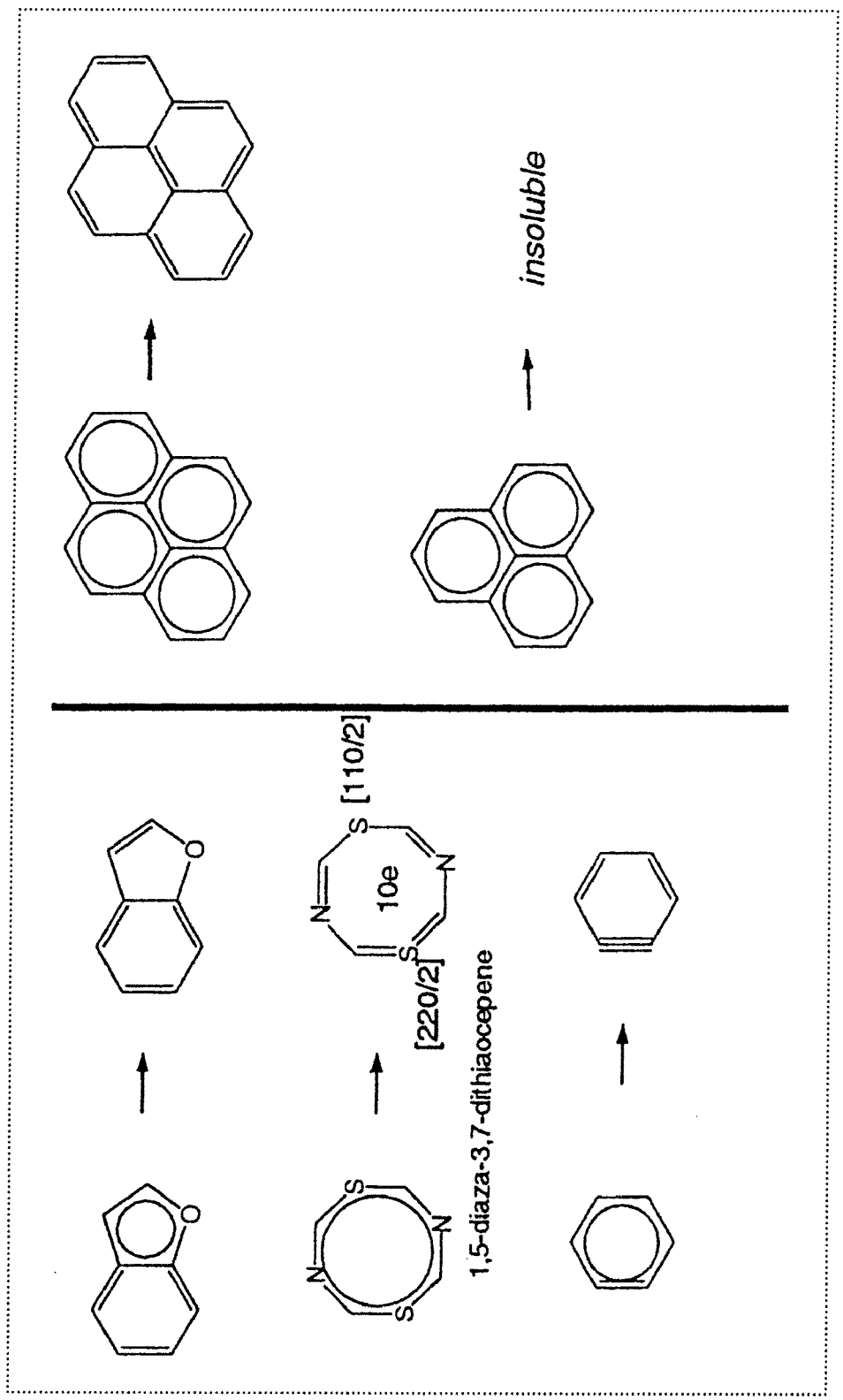

FIG. 15 shows an example of when an external bond is co-opted to serve as an additional internal single bond. In part a of FIG. 15, an atom has one fixed single bond, and its ESVD (for example, [121]) has just been assigned. Ordinarily the order of the next bond (marked by the arrow) would have to be double, but because the atom has three internal bonds, the order might also be single. In part b of FIG. 15, all of the nitrogen's bonds have been fixed but one. Normally no bond order could be chosen, because two internal bonds of the nitrogen's ESVD, [111], have been consumed. However, because the nitrogen's ICN is 3, the external bond may be reassigned as an internal (single) bond.

If either AddSingle or CooptExtern is set to true, b's order is set to single and any relevant state variables are updated (step 5100), and the Dispatcher is recursively invoked (step 5110). If the Dispatcher returns "Perfect Solution", the instant procedure returns the same (step 5120).

If AddDouble is set to true, b's order is set to double, updating any relevant state variables (step 5130), and the Dispatcher is recursively invoked (step 5140). If the Dispatcher returns "Perfect Solution", the instant procedure returns the same (step 5150).

Otherwise, the instant procedure returns "Keep Trying" (step 5150).

Figure 27:
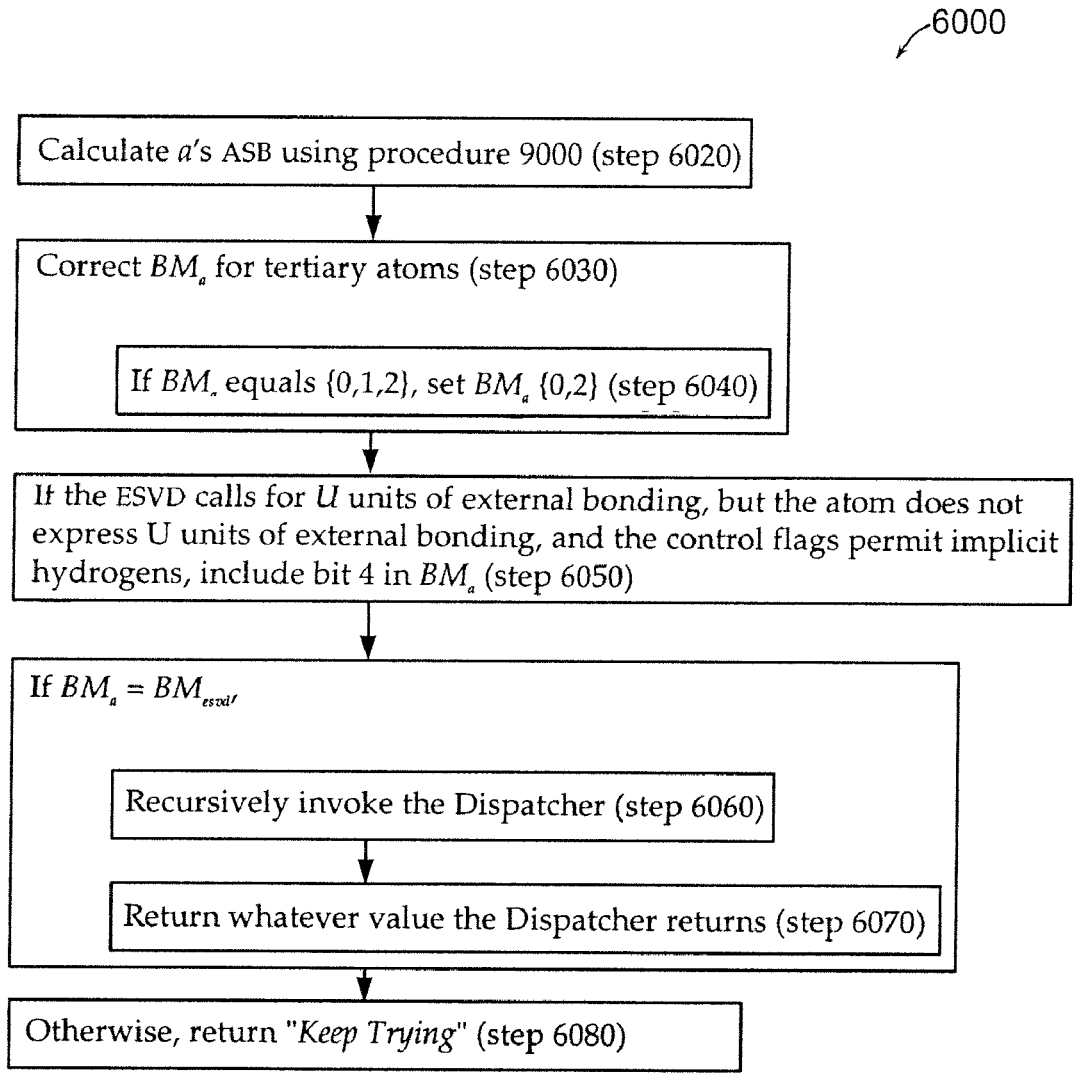

In procedure 6000 (FIG. 27), an atom is verified as complete. In particular, the procedure is provided with the state (S) and an atom (a), all the bonds of which have just been fixed. The procedure determines whether a's assigned ESVD is compatible with its bond orders, and returns "Perfect Solution" or "Keep Trying". In a specific implementation, the procedure executes as follows (steps 6020-6080). a's ASB is calculated using procedure 9000 (FIG. 30) (step 6020) and is called $BM_a$. $BM_{esvd}$ is set to the ESB of a's assigned ESVD. Only the bonding bits (0-5 of Table 3 of FIG. 11) of $BM_a$ and $BM_{esvd}$ are considered. $BM_a$ is corrected for tertiary atoms (step 6030), so that if $BM_a$ equals {0,1,2} (see Table 3 of FIG. 11), $BM_a$ is set instead to {0,2} (step 6040).

If the ESVD calls for U units of external bonding, but the atom does not express U units of external bonding, and the control flags permit implicit hydrogens, bit 4 is included in $BM_a$ (step 6050).

If $BM_a=BM_{esvd}$, the assigned ESVD is satisfactory. In this case, the Dispatcher is recursively invoked (step 6060), and the instant procedure returns whatever value the Dispatcher returns (step 6070).

Otherwise, the assigned ESVD is determined not to be viable, and "Keep Trying" is returned (step 6080).

Figure 28:
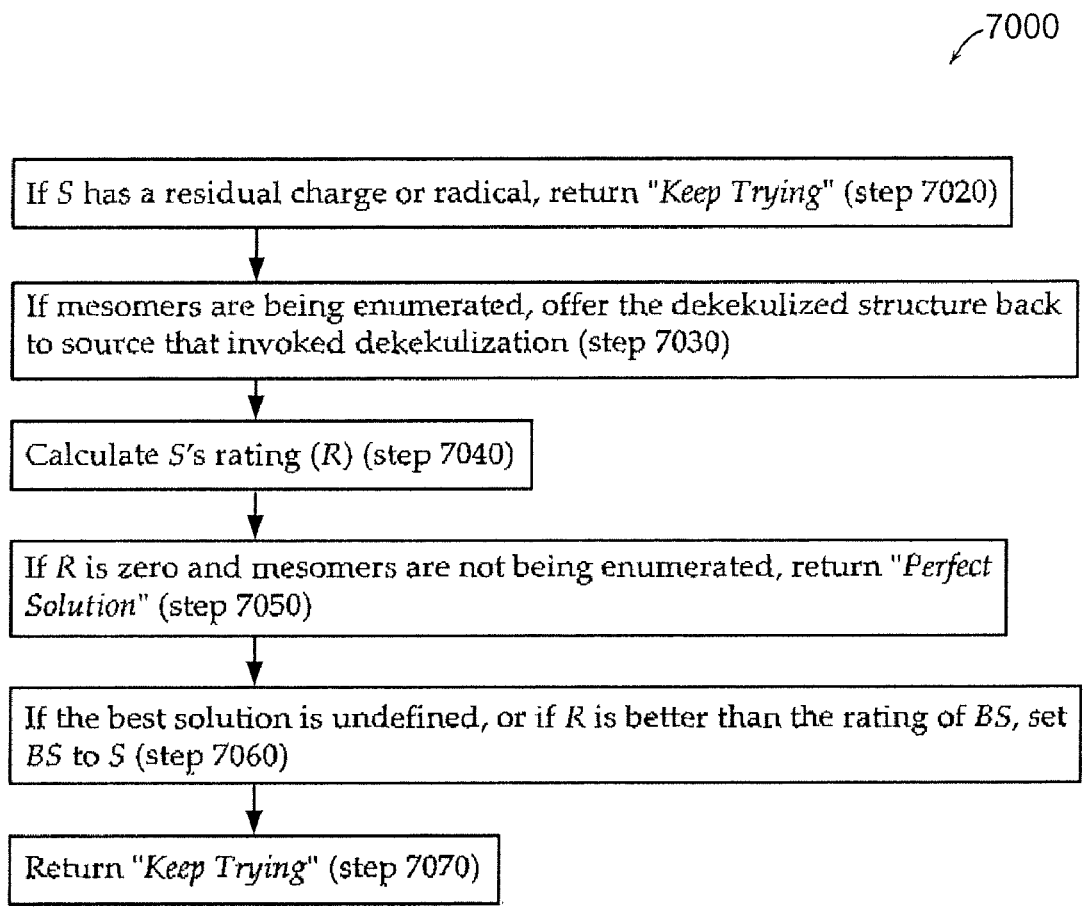

Procedure 7000 (FIG. 28), when provided with a state (S), which represents a complete traversal of the path, determines whether S offers a perfect solution, and returns "Perfect Solution" or "Keep Trying". If an imperfect solution is viable, it is noted. In a specific embodiment, the determination is executed as follows (steps 7020-7070). If S has a residual charge or radical, "Keep Trying" is returned (step 7020).

At this stage, S constitutes a viable solution.

If mesomers are being enumerated, the dekekulized structure may be offered, e.g., via a callback function, back to the client program or other source that invoked dekekulization (step 7030).

Figure 31A:
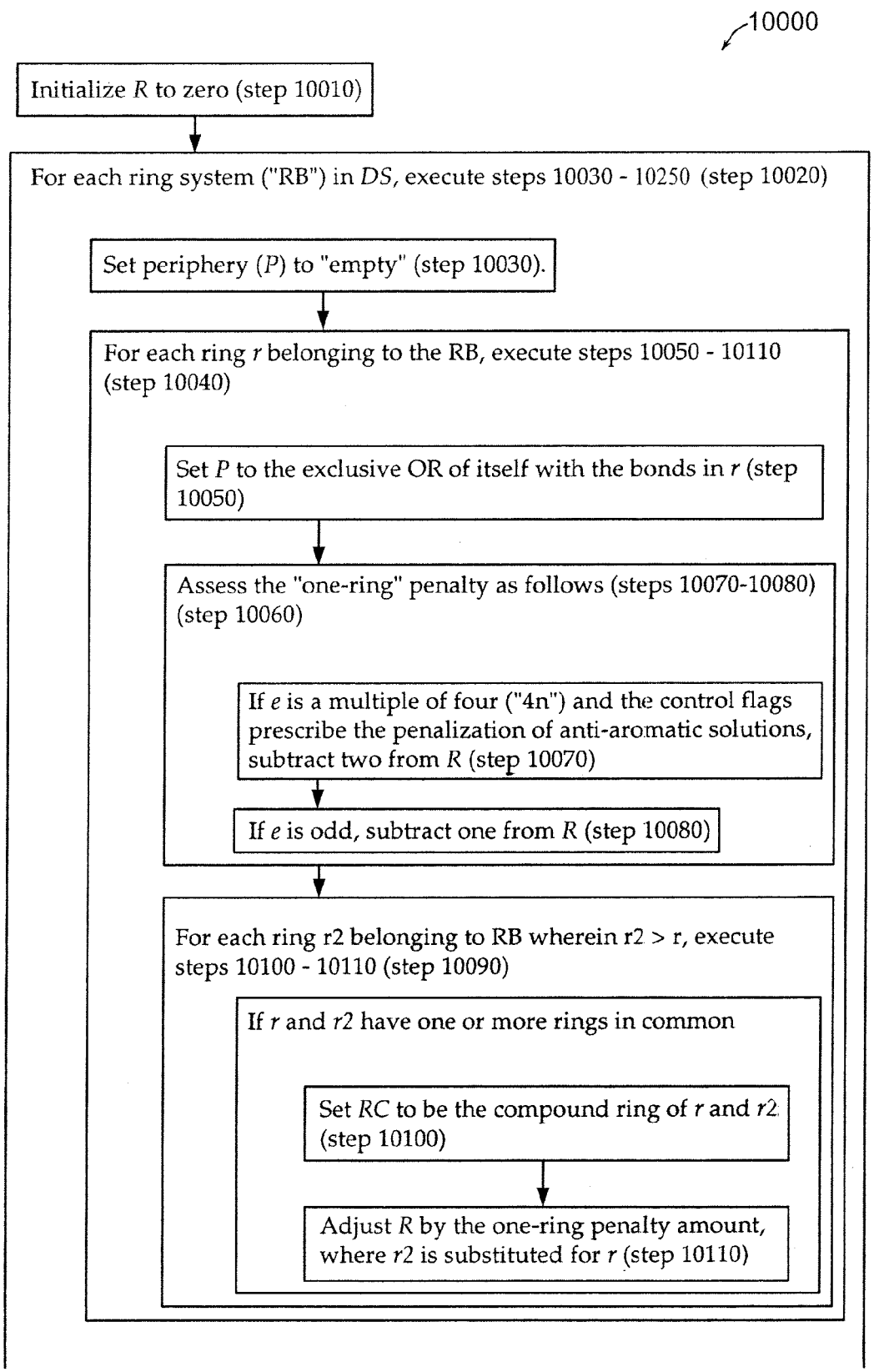
Figure 31B:
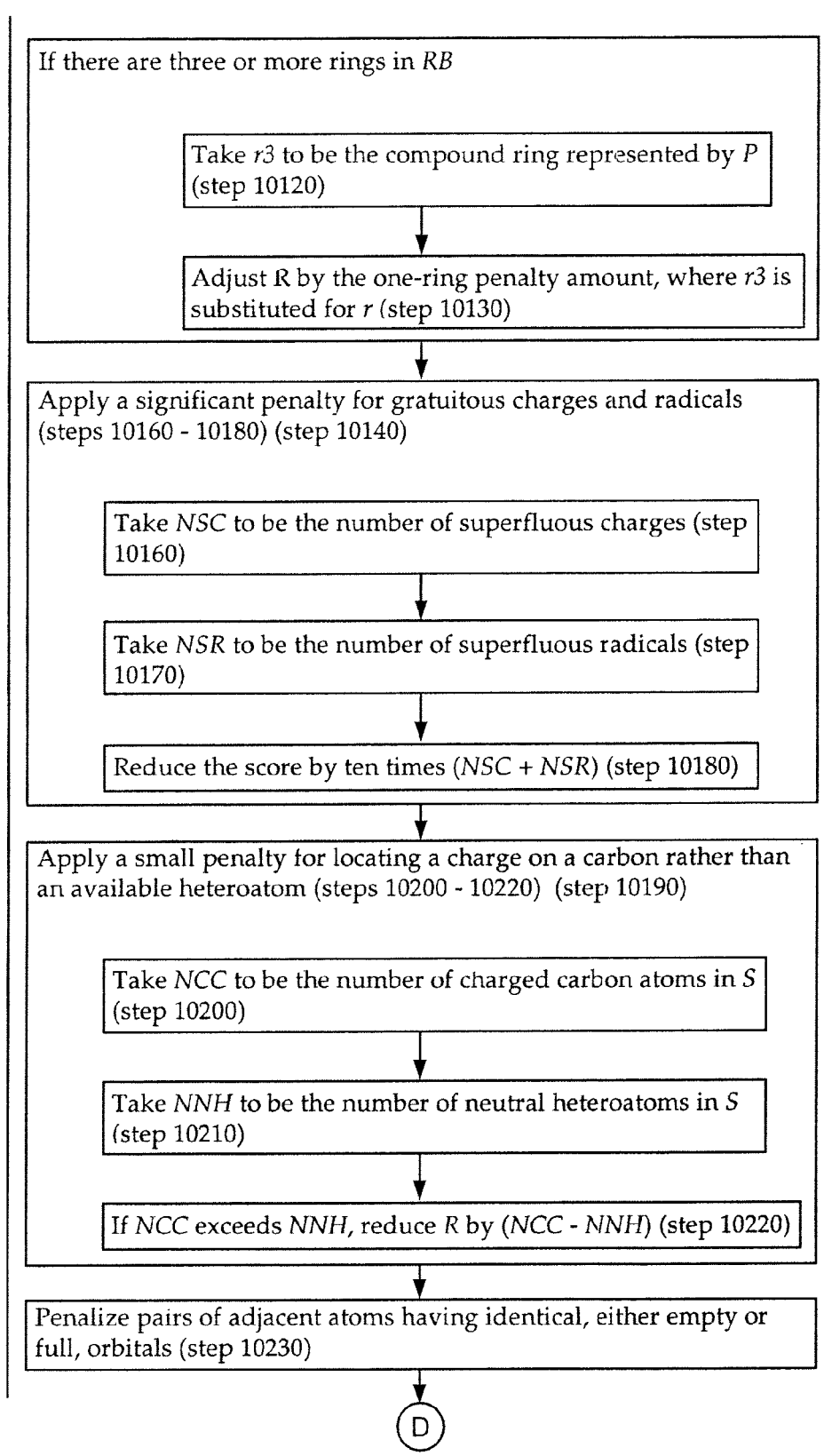
Figure 31C:
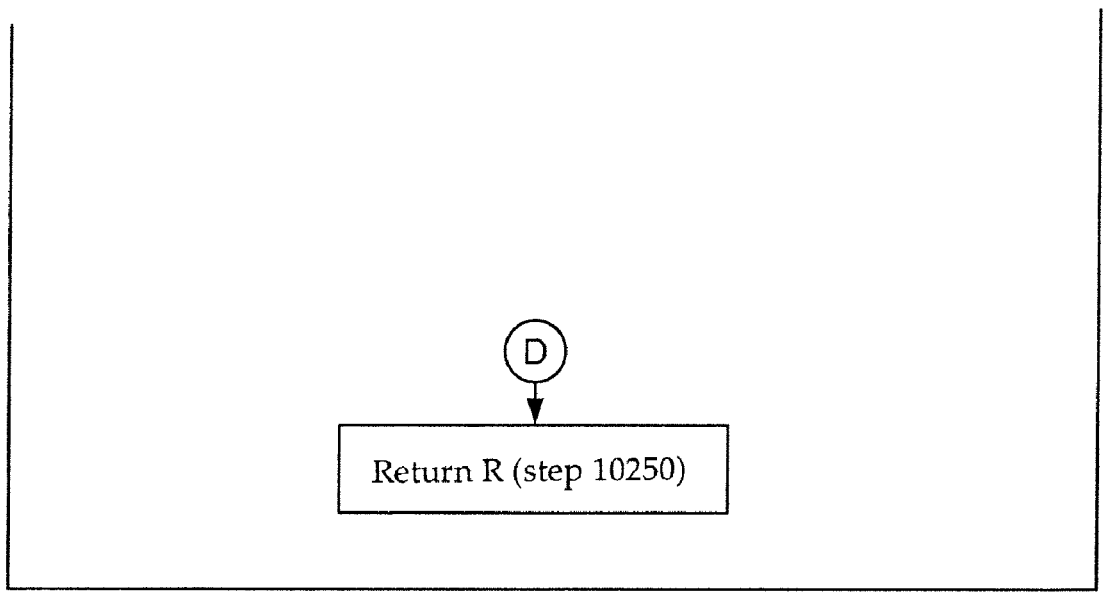

S's rating (R) is calculated by use of procedure 10000 (FIGS. 31A-31C) (step 7040). If R is zero, indicating a perfect solution, and mesomers are not being enumerated, "Perfect Solution" is returned (step 7050). If the best solution (BS, initialized in step 2130) is undefined, or if R is better than the rating of BS, BS is set to S (step 7060), and "Keep Trying" is returned (step 7070).

In procedure 8000 (FIG. 29), an ESB is calculated for an ESVD. Procedure 8000 is provided with an ESVD and returns the ESB (see Table 3 in FIG. 11 for bit descriptions). In a specific implementation, the calculation proceeds as follows (steps 8010-8060). ESB is initialized to zero (step 8010). The following bits of ESB are set according to the ESVD's charge (step 8020):

Neutral: {8,11,12}
Plus: {9,11}
Minus: {10,12}

The following bits are set according to the ESVD's radical character (step 8030):

Radical: {13}
Non-radical: {14}

The following bits are set according to the ESVD's pair of internal bond orders (step 8040):

Single, single: {0,1}
Single, double: {0,2}
Double, double: {2,3}

The following bits are set according to whether the ESVD has one or more units of external bonding (step 8050):

Has an external bond: {4}
Does not have an external bond: {5}

The ESB is returned (step 8060).

In procedure 9000 (FIG. 30), an ASB is calculated. Procedure 9000 is provided with an identification of an atom (a), some or all of the bonds of which may have been fixed, and the current state (S), and returns a's atom screening bitmask (ASB). (See Table 3 in FIG. 11 for bit descriptions.) In a specific implementation, procedure 9000 executes as follows (steps 9010-9090). ASB is initialized to zero (step 9010). The following bits of ASB are set according to the number of internal bonds adjacent to a that are fixed, with bond order single (step 9020):

One: {0}
Two or more: {0,1}

The following bits are set according to the number of internal bonds adjacent to a that are fixed, with bond order double (step 9030):

One: {2}
Two or more: {2,3}

If a has more than two adjacent bonds, bit {4} is set (step 9040). If a has exactly two adjacent bonds, and if the control flags dictate that no implicit hydrogens exist, and a's element type is not carbon (since carbons are always permitted implicit hydrogens in this implementation), bit {5} is set (step 9050). If the residual radical value of S is "no-radical", and the control flags do not permit unnecessary creation of radicals, bit {14} is set (step 9060).

If the residual charge of S is zero and the control flags do not permit unnecessary creation of charged atoms; or if a's element type is carbon and the control flags require charges to be situated on heteroatoms, bits {11,12} are set (step 9070); otherwise, if the residual charge of S is positive, bit {11} is set.

If the residual charge of S is negative, bit {12} is set (step 9080).

The ASB is returned (step 9090).

In procedure 10000 (FIGS. 31A-31C), a state is rated ("scored"). Procedure 10000 is provided with a state (S) that incorporates the entire path through the current delocalized system (DS), and returns an integer (R) that rates the quality of the solution. R is zero or negative, with zero reflecting a perfect solution, and less negative values being better than more negative ones. In a specific implementation, procedure 10000 executes as follows (steps 10010-10250). R is initialized to zero (step 10010).

For each ring system ("RB") in DS, the following steps 10030-10250 are executed (step 10020). Periphery (P), which is to become the set of bonds in the periphery of the ring system, is set to "empty" (step 10030). For each ring r belonging to the RB, the following steps 10050-10110 are executed (step 10040). P is set to the exclusive OR of itself with the bonds in r (step 10050). (Taking the exclusive OR of two sets produces a third set having the value zero where the corresponding bits in the two given sets match, i.e., 0=0 or 1=1, and one otherwise.) The "one-ring" penalty is assessed (step 10060) as follows (steps 10070-10080). Where e represents the number of pi electrons in r, e is the sum of the "electrons contributed" value of the ESVD (see Table 1 in FIG. 7) for each atom in r. If e is a multiple of four ("4n"), i.e., conventionally anti-aromatic, and the control flags prescribe the penalization of anti-aromatic solutions, two is subtracted from R (step 10070). If e is odd, one is subtracted from R (step 10080).

For each ring r2 belonging to RB wherein r2>r, the following steps 10100-10110 are executed (step 10090). If r and r2 have one or more rings in common, RC is set to be the compound ring of r and r2, i.e., the ring obtained by taking the exclusive OR of the bonds in r and r2 (step 10100) and R is adjusted by the one-ring penalty amount assessed in steps 10060-10080, where r2 is substituted for r, (step 10110).

If there are three or more rings in RB, r3 is taken to be the compound ring represented by P (step 10120), and R is adjusted by the one-ring penalty amount assessed in steps 10060-10080, where r3 is substituted for r (step 10130).

A significant penalty is applied for gratuitous charges and radicals (step 10140), as follows (steps 10160-10180). NSC is taken to be the number of superfluous charges, calculated from:

NSC=(number of cations in $S$+number of anions in $S$)−|C| where |C| is the absolute value of DS's net charge (step 10160). NSR is taken to be the number of superfluous radicals, calculated from:

NSR=number of radical atoms in $S$−Q where Q is zero if DS has an even number of unpaired electrons, and one otherwise (step 10170). The score is reduced by ten times (NSC+NSR) (step 10180).

A small penalty is applied for locating a charge on a carbon rather than an available heteroatom (step 10190), as follows (steps 10200-10220). NCC is taken to be the number of charged carbon atoms in S (step 10200). NNH is taken to be the number of neutral heteroatoms in S (step 10210). If NCC exceeds NNH, R is reduced by (NCC−NNH) (step 10220).

Pairs of adjacent atoms having identical, either empty or full, orbitals are penalized (step 10230). For example, in at least some cases, it is not desirable for two [111/0] boron atoms, or two [111/2] (pyrrole-type) nitrogen atoms, to be adjacent. For each pair of adjacent atoms in DS, five is substracted from R if the atoms in the pair have the same pi electron contribution (see Table 1 in FIG. 7) which is not one.

R is returned (step 10250).

Figure 19:
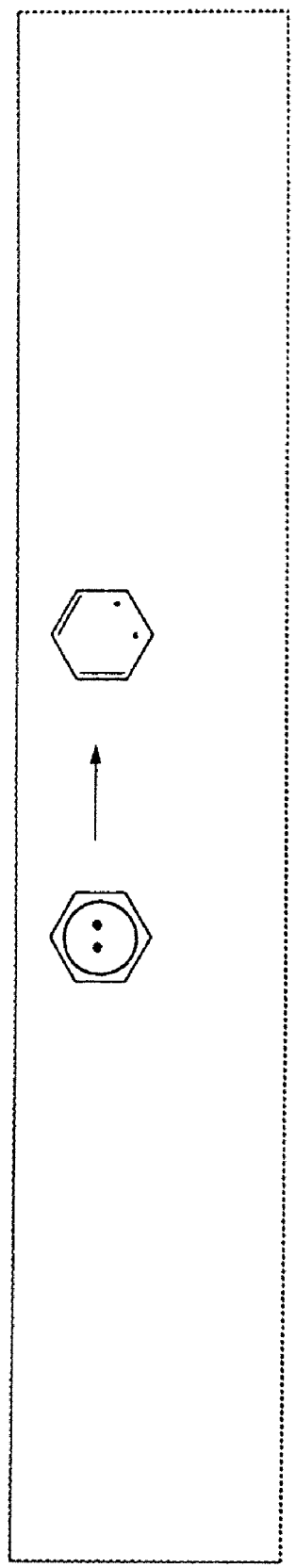
Figure 20:
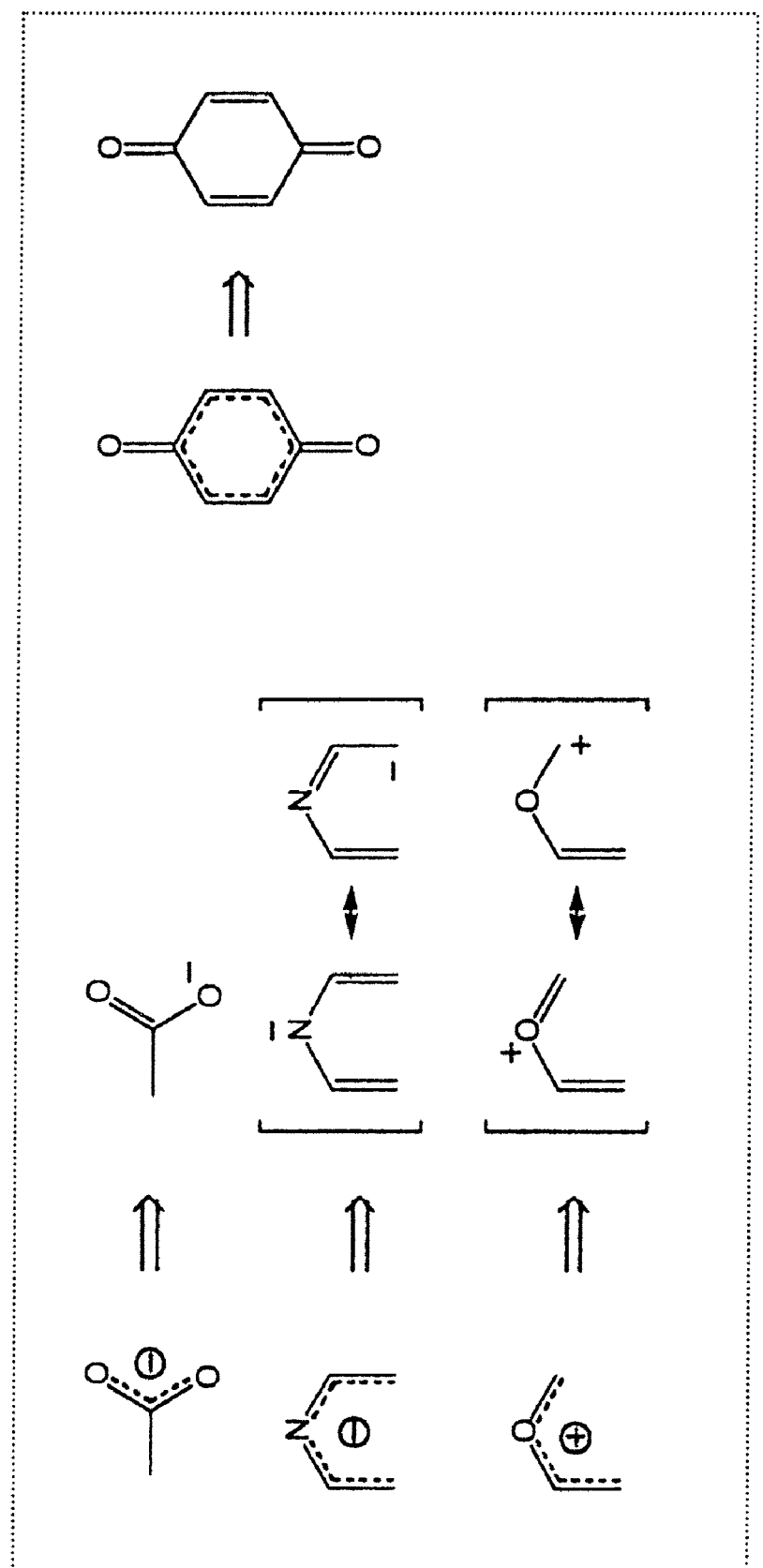

FIGS. 16-20 illustrate examples related to the procedures described above. FIGS. 19 and 20 illustrate radical structures and acyclic examples, respectively.

All or a portion of the procedures described above may be implemented in hardware or software, or a combination of both. In at least some cases, it is advantageous if the technique is implemented in computer programs executing on one or more programmable computers, such as a personal computer running or able to run an operating system such as UNIX, Linux, Microsoft Windows 95, 98, 2000, or NT, or MacOS, that each include a processor, a storage medium readable by the processor (including volatile and non-volatile memory and/or storage elements), at least one input device such as a keyboard, and at least one output device. Program code is applied to data entered using the input device to perform the technique described above and to generate output information. The output information is applied to one or more output devices such as a display screen of the computer.

In at least some cases, it is advantageous if each program is implemented in a high level procedural or object-oriented programming language such as Perl, C, C++, or Java to communicate with a computer system. However, the programs can be implemented in assembly or machine language, if desired. In any case, the language may be a compiled or interpreted language.

In at least some cases, it is advantageous if each such computer program is stored on a storage medium or device, such as ROM or optical or magnetic disc, that is readable by a general or special purpose programmable computer for configuring and operating the computer when the storage medium or device is read by the computer to perform the procedures described in this document. The system may also be considered to be implemented as a computer-readable storage medium, configured with a computer program, where the storage medium so configured causes a computer to operate in a specific and predefined manner.

Figure 21:
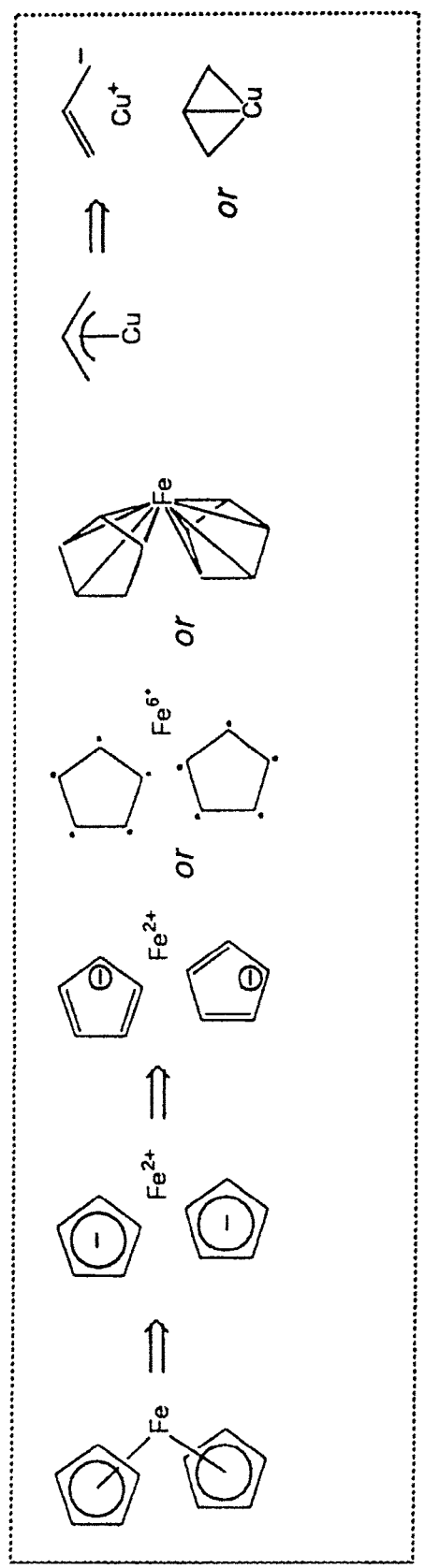

Other embodiments are within the scope of the following claims. For example, one or more of the procedures described above may be applied to structures other than common organic structures. For example, benzynes and other systems, cyclic and acyclic, contain one or more bonds involving pi orbitals that are not delocalized. These cases may be treated by formally assigning the pi bond to the external bonding network, as if each of the pair of atoms had an external attachment instead of an internal bond. In another example, charges localized in a sigma orbital (as in PhLi) may be ignored, as may be localized radicals. Another example involves multi-center bonds ("$\mu$ bonds"). Many organometallic compounds, such as ferrocene and allyl copper (see FIG. 21 which illustrates multi-center bonds), are depicted in the delocalized representation with a bond between an atom, usually a metal, and a pi network, rather than another atom. Effectively, no aesthetic representation exists for these structures that eliminates the multi-center bond. More particularly, in at least some cases, in order to fix the bonding in the delocalized system (cyclopentadienyl, ally), either charge or unpaired electrons or "exhaustive sigma" bonds must be introduced.

What is claimed is:

1. A computer-implemented method for use in deriving fixed bond information, comprising:
   analyzing a delocalized representation of a chemical structure;
   identifying, based on valence information, a plurality of fixed bond representation candidates for at least a portion of the chemical structure;
   evaluating at least a subset of the fixed bond representation candidates;
   selecting from among the plurality of fixed bond representation candidates one or more candidates based on the evaluation;
   producing fixed bond information based on the selection; and
   outputting the produced fixed bond information to an output device.

2. The computer-implemented method of claim 1, wherein the identifying includes tracing a path through the structure, assigning bond orders and atomic charges or radicals as the path is traced, and, when an unacceptable state is detected, backtracking the path to the last assignment that was made.

3. The computer-implemented method of claim 1, further comprising:
   deriving electronic state and valence distributions information together with analyzing the delocalized representation.

4. The computer-implemented method of claim 1, further comprising:
   determining, by either exhaustion or exceeding a predetermined amount of time, whether it is possible to produce a neutral, non-radical fixed bond representation of most chemical structures.

5. The computer-implemented method of claim 1, wherein when the evaluating determines that a fixed bond representation candidate cannot be improved upon, it is selected.

6. The computer-implemented method of claim 1, wherein the assigning atomic charges or radicals is performed based on electronic state and valence distribution (ESVD), and further comprising:

queuing at least a subset of the ESVDs by priority.

7. The computer-implemented method of claim 6, wherein the highest priority ESVD is assigned and the remainder of the at least a subset of the ESVDs are placed in an independent queue.

8. A method for use in deriving fixed bond information, comprising:

analyzing a delocalized representation of a chemical structure;

identifying, based on valence information, a plurality of fixed bond representation candidates for at least a portion of the chemical structure;

evaluating at least a subset of the fixed bond representation candidates;

selecting from among the plurality of fixed bond representation candidates based on the evaluation;

producing fixed bond information based on the selection;

using a precomputed collection of atom valences as a function of element, charge, radical state, and number and distribution of bonds inside and outside of a delocalized region in the delocalized representation; and outputting the produced fixed bond information to an output device.

9. The method of claim 8, wherein the identifying includes tracing a path through the structure, assigning bond orders and atomic charges or radicals as the path is traced, and backtracking the path to the last assignment that was made, when an unacceptable state is detected.

10. The method of claim 8, wherein the collection is configured to allow additional elements and values to be added.

11. The method of claim 8, wherein the collection is configured to allow additional elements and values to be added to apply to any chemical element.

12. A computer-implemented system for deriving fixed bond information, comprising:

an analyzer configured to analyze a delocalized representation of a chemical structure;

an identifier configured to identify, based on valence information, a plurality of fixed bond representation candidates for at least a portion of the chemical structure;

an evaluator configured to evaluate at least a subset of the fixed bond representation candidates;

a selector configured to elect from among the plurality of fixed bond representation candidates based on the evaluation; and a producer configured to produce and output fixed bond information based on the selection.

13. The computer-implemented system of claim 12, the identifier configured to identify the plurality of fixed bond representation candidates for at least a portion of the chemical structure further based on tracing a path through the structure, assigning bond orders and atomic charges or radicals as the path is traced, and, when an unacceptable state is detected, backtracking the path to the last assignment that was made.

14. Computer software, residing on a non-transitory computer-readable storage medium, comprising a set of instructions for use in a computer system to help cause the computer system to derive fixed bond information, the instructions causing the system to:

analyze a delocalized representation of a chemical structure;

identify, based on valence information, a plurality of fixed bond representation candidates for at least a portion of the chemical structure;

evaluate at least a subset of the fixed bond representation candidates;

select from among the plurality of fixed bond representation candidates based on the evaluation;

produce fixed bond information based on the selection; and output the produced fixed bond information to an output device.

15. The computer software of claim 14, wherein the identifying includes tracing a path through the structure, assigning bond orders and atomic charges or radicals as the path is traced, and backtracking the path to the last assignment that was made, when an unacceptable state is detected.

* * * * *